United States Patent
Guirola Cruz et al.

(10) Patent No.: US 11,013,235 B2
(45) Date of Patent: May 25, 2021

(54) METHOD FOR TREATING DISEASES IN PLANTS

(71) Applicant: Centro de Ingeniería Genética y Biotecnología, Havana (CU)

(72) Inventors: Osmany Guirola Cruz, Havana (CU); Orlando Borrás Hidalgo, Havana (CU); Luis Javier González López, Havana (CU); Raimundo Ubieta Gómez, Havana (CU); Eulogio Pimentel Vázquez, Havana (CU); Merardo Pujol Ferrer, Havana (CU)

(73) Assignee: Centro de Ingeniería Genética y Biotecnología, Havana (CU)

( * ) Notice: Subject to any disclaimer, the term of this patent is extended or adjusted under 35 U.S.C. 154(b) by 0 days.

(21) Appl. No.: 16/752,214

(22) Filed: Jan. 24, 2020

(65) Prior Publication Data

US 2020/0288720 A1 Sep. 17, 2020

Related U.S. Application Data

(63) Continuation of application No. 15/747,237, filed as application No. PCT/CU2016/050001 on Aug. 1, 2016.

(30) Foreign Application Priority Data

Jul. 31, 2015 (CU) .................................. 2015-0077

(51) Int. Cl.
*A01N 43/90* (2006.01)
*A01N 43/40* (2006.01)
(Continued)

(52) U.S. Cl.
CPC ............. *A01N 43/90* (2013.01); *A01N 43/40* (2013.01); *A01N 43/60* (2013.01); *A01N 43/84* (2013.01);
(Continued)

(58) Field of Classification Search
CPC ........ A01N 43/40; A01N 43/60; A01N 43/84; A01N 43/90; C07D 265/36; C07D 401/12;
(Continued)

(56) References Cited

U.S. PATENT DOCUMENTS 8,618,149 B2 12/2013 Melander et al.
9,247,749 B2 2/2016 Wang et al.
(Continued)

FOREIGN PATENT DOCUMENTS

CN 102067850 A 5/2011
WO 0167867 A2 9/2001

OTHER PUBLICATIONS

Christensen, L. P., "Polyphenols in Chronic Diseases and their Mechanisms of Action," in Polyphenols in Human Health and Disease, (2014).
(Continued)

*Primary Examiner* — Sabiha N Qazi
(74) *Attorney, Agent, or Firm* — Hoffmann and Baron, LLP

(57) ABSTRACT

The following invention discloses a method for the control of plant diseases wherein a composition comprising a compound having the structure represented by one of the formulas from I to V, (Continued)

-continued (V)

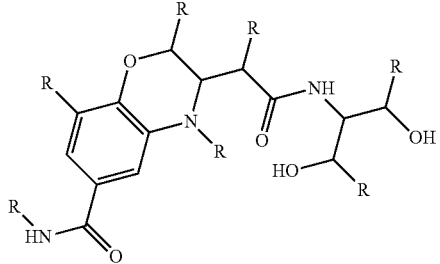

is applied to the plants. It also discloses the use of said compounds, or their salts for the stimulation of the natural defense and the induction of resistance against plant diseases. Moreover, it comprises the use of said compounds of structure represented by one of the formulas from I to V for the preventive or curative treatment of said diseases. A composition for agriculture, comprising a compound having the structure represented by one of the formulas from I to V, is also part of the invention.

17 Claims, 3 Drawing Sheets

Specification includes a Sequence Listing.

(51) Int. Cl.
| | |
|---|---|
| A01N 43/60 | (2006.01) |
| A01N 43/84 | (2006.01) |
| C07D 265/36 | (2006.01) |
| C07D 401/12 | (2006.01) |
| C07D 403/06 | (2006.01) |
| C07D 413/12 | (2006.01) |
| C07D 493/04 | (2006.01) |
| C07D 495/04 | (2006.01) |

(52) U.S. Cl.
CPC ......... *C07D 265/36* (2013.01); *C07D 401/12* (2013.01); *C07D 403/06* (2013.01); *C07D 413/12* (2013.01); *C07D 493/04* (2013.01); *C07D 495/04* (2013.01)

(58) Field of Classification Search
CPC .......................... C07D 403/06; C07D 413/12; C07D 493/04; C07D 495/04
USPC ...................................................... 530/250
See application file for complete search history.

(56) References Cited

U.S. PATENT DOCUMENTS

| 9,521,850 B2 | 12/2016 | Wang et al. |
| 10,104,889 B2 | 10/2018 | Hidalgo et al. |
| 2002/0164797 A1 | 11/2002 | Martin et al. |
| 2012/0328677 A1 | 12/2012 | Kudsi et al. |
| 2014/0171326 A1 | 6/2014 | Hidalgo et al. |
| 2015/0087512 A1 | 3/2015 | Wang et al. |

OTHER PUBLICATIONS

Gao, Al-Guo, et al., "Fungal Pathogen Protection in Potato by Expression of a Plant Defensin Peptide," Nature Biotechnology, 18.12, p. 1307 (2002).
Baker, B. et al., "Signaling in Plant-Microbe Interactions," Science 276.5313, pp. 726-733 (1997).
Fritig, B., et al., "Antimicrobial Proteins in Induced Plant Defense," Current Opinion in Immunology, 10.1, pp. 16-22, (1996).
Legrand, M., et al., "O-diphenol O-Methyltransferases of Healthy and Tobacco-Mosaic-Virus-Infected Hypersensitive Tobacco," Planta 144.1, pp. 101-108, (1978).
Cordelier, S., et al., Biological and Molecular Comparison Between Localized and Systemic Acquired Resistance Induced in Tobacco by a Phytophthora Megasperma glycoprotein elicitin. Plant Molecular Biology, 51(1), pp. 109-118 (2003).
Borras-Hidalgo, O., et al., "A Gene for Plant Protection: Expression of a Bean Polygalacturonase Inhibitor in Tobacco Confers a Strong Resistance Against Rhizoctonia Solani and Two Oomycetes," Frontiers in Plant Science, V.3, Article 268, (Dec. 2012).
Martin, J. T., "The Fungitoxicities of Plant Furocoumarins," Annals of Applied Biology, 57(3), 501-508 (1966).
Database Chemcats [Online], Apr. 7, 2016, XP002765302, Database Accession No. 1560323453.
Database Chemcats [Online], Dec. 1, 2016, XP002765303. Database Assession No. 0050406260.
Database Registry [Online], Chemical Abstracts Service, Columbus Ohio, US, Feb. 7, 2007, XP002765304, Database Accession No. 919734-07-9.
Database Registry [Online], Chemical Abstracts Service, Columbus Ohio, US, Mar. 5, 2007, XP002765305, Database Accession No. 924807-39-6.
Database Chemcats [Online], Dec. 1, 2016, XP002765306, Database Accession No. 1658920895.
Database Chemcats [Online], Apr. 7, 2016, XP002765307, Database Accession No. 0949549927.
Database Chemcats [Online], Apr. 7, 2016, XP002765308, Database Accession No. 1442893514.
Database Chemcats [Online], Dec. 1, 2016, XP002765309, Database Accession No. 0500768801.
Database Registry [Online], Chemical Abstracts Service, Columbus Ohio, US: Feb. 15, 2007, XP002765310, Database Accession No. 921063-14-1.
Staskawicz, B. J. "Genetics of Plant-Pathogen Interactions Specifying Plant Disease Resistance," Plant Physiology, 125(1), 73-76, (2001).

A

B

C

A

B

SEQUENCE LISTING

```
<160> NUMBER OF SEQ ID NOS: 16

<210> SEQ ID NO 1
<211> LENGTH: 19
<212> TYPE: DNA
<213> ORGANISM: Artificial Sequence
<220> FEATURE:
<223> OTHER INFORMATION: Description: Arabidopsis thaliana gene
      detection Oligonucleotide
```

<400> SEQUENCE: 1
gatgtgccaa agtgaggtg                                                19

<210> SEQ ID NO 2
<211> LENGTH: 22
<212> TYPE: DNA
<213> ORGANISM: Artificial Sequence
<220> FEATURE:
<223> OTHER INFORMATION: Description: Arabidopsis thaliana gene
      detection Oligonucleotide

<400> SEQUENCE: 2
tgcatgatca catcattact tc                                            22

<210> SEQ ID NO 3
<211> LENGTH: 19
<212> TYPE: DNA
<213> ORGANISM: Artificial Sequence
<220> FEATURE:
<223> OTHER INFORMATION: Description: Arabidopsis thaliana gene
      detection Oligonucleotide

<400> SEQUENCE: 3
tggcttctga ccacttcac                                                19

<210> SEQ ID NO 4
<211> LENGTH: 20
<212> TYPE: DNA
<213> ORGANISM: Artificial Sequence
<220> FEATURE:
<223> OTHER INFORMATION: Description: Arabidopsis thaliana gene
      detection Oligonucleotide

<400> SEQUENCE: 4
acgctcgtcg aagagtttct                                               20

<210> SEQ ID NO 5
<211> LENGTH: 20
<212> TYPE: DNA
<213> ORGANISM: Artificial Sequence
<220> FEATURE:
<223> OTHER INFORMATION: Description: Arabidopsis thaliana gene
      detection Oligonucleotide

<400> SEQUENCE: 5
tcatggctaa gtttgcttcc                                               20

<210> SEQ ID NO 6
<211> LENGTH: 20
<212> TYPE: DNA
<213> ORGANISM: Artificial Sequence
<220> FEATURE:
<223> OTHER INFORMATION: Description: Arabidopsis thaliana gene
      detection Oligonucleotide

<400> SEQUENCE: 6
tgtcccactt ggcttctcgc                                               20

<210> SEQ ID NO 7
<211> LENGTH: 19
<212> TYPE: DNA
<213> ORGANISM: Artificial Sequence
<220> FEATURE:
<223> OTHER INFORMATION: Description: Arabidopsis thaliana gene
      detection Oligonucleotide

<400> SEQUENCE: 7

```
cagaactttg gccgactac                                               19
```

```
<210> SEQ ID NO 8
<211> LENGTH: 19
<212> TYPE: DNA
<213> ORGANISM: Artificial Sequence
<220> FEATURE:
<223> OTHER INFORMATION: Description: Arabidopsis thaliana gene
      detection Oligonucleotide

<400> SEQUENCE: 8
atggtctttc cggtgagag                                               19
```

```
<210> SEQ ID NO 9
<211> LENGTH: 22
<212> TYPE: DNA
<213> ORGANISM: Artificial Sequence
<220> FEATURE:
<223> OTHER INFORMATION: Description:  PAL gene detection
      Oligonucleotide

<400> SEQUENCE: 9
aacgggttgc cttcaaatct ta                                           22
```

```
<210> SEQ ID NO 10
<211> LENGTH: 22
<212> TYPE: DNA
<213> ORGANISM: Artificial Sequence
<220> FEATURE:
<223> OTHER INFORMATION: Description:  PAL gene detection
      Oligonucleotide

<400> SEQUENCE: 10
acatgattgg tgacaggatt gg                                           22
```

```
<210> SEQ ID NO 11
<211> LENGTH: 19
<212> TYPE: DNA
<213> ORGANISM: Artificial Sequence
<220> FEATURE:
<223> OTHER INFORMATION: Description: Lyase gene detection
      Oligonucleotide

<400> SEQUENCE: 11
ccacacttgg ctcggatgc                                               19
```

```
<210> SEQ ID NO 12
<211> LENGTH: 18
<212> TYPE: DNA
<213> ORGANISM: Artificial Sequence
<220> FEATURE:
<223> OTHER INFORMATION: Description: Lyase gene detection
      Oligonucleotide

<400> SEQUENCE: 12
cgtgcggagc aatggttc                                                18
```

```
<210> SEQ ID NO 13
<211> LENGTH: 20
<212> TYPE: DNA
<213> ORGANISM: Artificial Sequence
<220> FEATURE:
<223> OTHER INFORMATION: Description:  Actin gene detection
      Oligonucleotide

<400> SEQUENCE: 13
```

-continued

```
gtggctccac cagagagaaa                                                  20

<210> SEQ ID NO 14
<211> LENGTH: 20
<212> TYPE: DNA
<213> ORGANISM: Artificial Sequence
<220> FEATURE:
<223> OTHER INFORMATION: Description:  Actin gene detection
      Oligonucleotide

<400> SEQUENCE: 14
tggatggacc agactcatca                                                  20

<210> SEQ ID NO 15
<211> LENGTH: 21
<212> TYPE: DNA
<213> ORGANISM: Artificial Sequence
<220> FEATURE:
<223> OTHER INFORMATION: Description:  Quantification Oligonucleotide

<400> SEQUENCE: 15
ctaatcccca aaagccatct c                                                21

<210> SEQ ID NO 16
<211> LENGTH: 20
<212> TYPE: DNA
<213> ORGANISM: Artificial Sequence
<220> FEATURE:
<223> OTHER INFORMATION: Description:  Quantification Oligonucleotide

<400> SEQUENCE: 16
cttcaggcaa aaccaactcc                                                  20
```

METHOD FOR TREATING DISEASES IN PLANTS

This application is a continuation of and applicant claims priority from U.S. patent application Ser. No. 15/747,237, filed on Jan. 24, 2018, which is the U.S. National Phase of International Patent Application Number PCT/CU2016/050001 filed Aug. 1, 2016, which claims priority from CU2015-0077 filed Jul. 31, 2015, each of which is incorporated herein by reference.

FIELD OF THE INVENTION

The present invention is related to the field of agricultural biotechnology, specifically to the use of furocoumarins for stimulating the natural defense and inducing disease resistance in plants. When the furocoumarins are applied, high levels of protection against plant diseases are obtained.

PREVIOUS ART

In recent decades many studies have been made about plant—pathogen interactions, from morphological, physiological, biochemical and molecular point of view. However, the results achieved up to date do not meet the needs and knowledge of the major research groups in the world, and high yields through a stable and efficient protection of crops is not accomplished. Despite the numerous measures taken globally for an integrated crop protection, major crop losses due to diseases reaching 80% of production are reported each year, specifically in situations where epidemics occur (Gao et al. (2000) Nature Biotechnol. 18: 1307-1310).

Plants and pathogens have co-evolved over millions of years. During this interaction, strategies have emerged that allow plants to recognize potential invading pathogens and trigger a successful defense. Likewise, pathogens have developed mechanisms that enable them to evade and/or suppress plant defense responses. The influence of this selective pressure on plants has led to the improvement of their defense mechanisms. As a result, the success of the pathogen to cause disease, far from being the rule is an exception (Staskawicz (2001) Plant Physiology 125: 73-76).

The perception of specific and general elicitors by plants not only allows the recognition of pathogens, but allows the transduction of signals for the activation of response mechanisms. Among the various signaling pathways activated are those mediated by intermediates such as reactive oxygen, salicylic acid, ethylene and jasmonic acid. The crossover between these phytohormone signaling pathways provides a regulatory potential that allow activation of an optimal combination of responses depending on the specific pathogen. The expression of genes related to pathogenicity (PR) and the synthesis of antimicrobial compounds that are generally phytoalexins, defensins, phenolics and flavonoids produced to directly attack the pathogen are also activated (Baker et al. (1997) Science 276: 726-733).

There are other response mechanisms that operate in plants, whose effects persist for a relatively long period of time after infection. These are called: acquired localized response and systemic acquired response. Acquired localized response is observed in a ring of cells, 5-10 mm thick, about injuries caused by the hypersensitive response. This area is characterized by a large accumulation of pathogenesis-related proteins, mainly basic (Fritig et al. (1998) Current Opinion of Immunology 10: 16-22) and stimulation of enzymes such as methyltransferases (Legrand et al. (1978) Planta 144: 101-108), the phenylpropanoid pathway, which is involved in the production of antibiotics such as scopoletin, which does not provide a suitable environment for pathogens, preventing their spread throughout the plant.

Systemic acquired response gives the plant a higher level of resistance against a subsequent infection of the same pathogen. It develops not only in infected tissues, but throughout the plant. It is characterized by the accumulation of PR proteins, particularly acidic, which are related to the signaling mechanism of salicylic acid (Cordelier et al. (2003) Plant Molecular Biology 51: 109-118).

An important problem that persists in agriculture is the insufficient control of plant diseases, which limit the agricultural production each year, worldwide. Therefore, in spite of the advances made, it is necessary to identify new compounds that could be useful for the induction of resistance to plant diseases, to achieve a more effective control of them.

DESCRIPTION OF THE INVENTION

The invention contributes to solve the problem mentioned above disclosing effective compounds for the stimulation of the natural defense and the induction of resistance to plant diseases. In this way, the invention provides a method for the treatment or prevention of plant diseases wherein an effective amount of a composition comprising at least a compound of structure represented by one of the formulas I to V

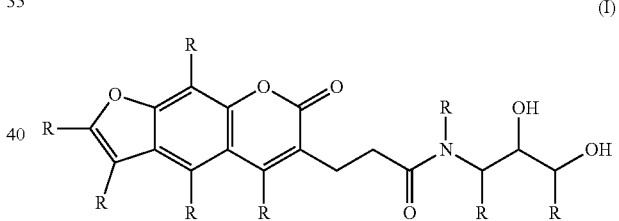

(I)

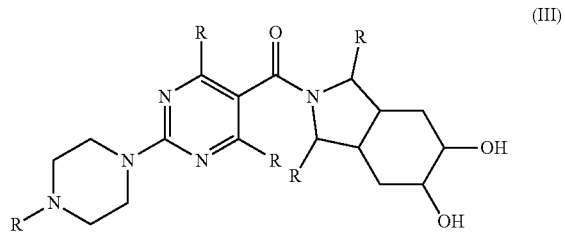

(III)

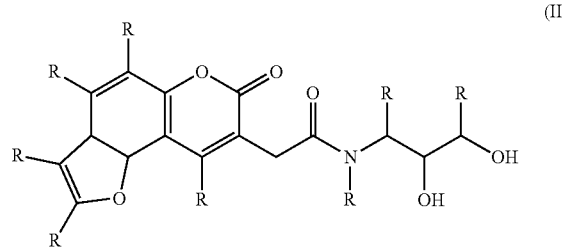

(II)

-continued

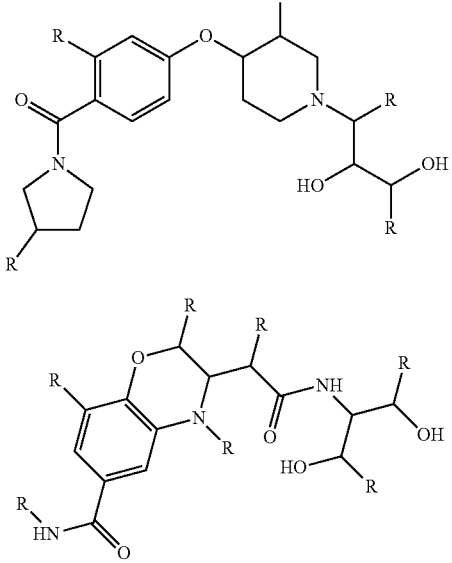

(IV)

(V)

R is one or more substituents selected from the group consisting of hydrogen, hydroxyl, halogen, alkyl $C_{1-12}$, heteroalkyl $C_{1-12}$, cycloalkyl $C_{3-7}$, heterocycloalkyl $C_{3-7}$, aryl, heteroaryl, arylalkyl $C_{1-3}$, heteroarylalkyl $C_{1-3}$, arylcycloalkyl $C_{1-7}$, heteroarylcycloalkyl $C_{1-7}$, alkyl $C_{1-3}$cycloalkyl $C_{3-7}$, and heteroalkyl $C_{1-3}$ cycloalkyl $C_{3-7}$, or their salts is applied to the plants.

Definitions

The term "alkyl" refers to an aliphatic hydrocarbon radical with a straight (i.e. unbranched) or branched chain having a defined number of carbon atoms (i.e. "alkyl C1-C10" corresponds to an alkyl which may be constituted by one to ten carbon atoms). The alkyl radical may be fully saturated, mono- or polyunsaturated and may contain di- and multivalent radicals. Examples of saturated hydrocarbon radicals include, but are not limited to, groups such as methyl, ethyl, n-propyl, isopropyl, 2,3-dimethylbutyl and others. Examples of unsaturated hydrocarbon radicals include, but are not limited to, groups such as vinyl, 2-propenyl, 2-butadienyl, 1,4-hexadienyl, 1,3-pentadienyl, ethynyl, 3-propynyl, 3-butynyl, 2,4-pentadienyl and others. Note that the term "alkyl" as used here, include divalent aliphatic hydrocarbon radicals with a straight or branched chain. Examples of divalent alkyl radicals include, but are not limited to, —CH2CH2CH2CH2-; —CH2CH=CHCH2-; —CH2C≡CCH2-; —CH2CH2CH(CH2CH2CH3)CH2- and others.

The term "heteroalkyl" by itself or in combination with another term, refers to an aliphatic hydrocarbon radical with a straight (i.e. unbranched) or branched chain consisting of at least one carbon atom and at least one heteroatom selected from the following: O, N, P, Si and S. The heteroatoms in the heteroalkyl radical may be equal or different. The heteroatom may be placed at any interior position of the heteroalkyl group or at the position at which alkyl group is attached to the remainder of the molecule. The heteroalkyl radical may be fully saturated, mono- or polyunsaturated and can included di- and multivalent radicals. Examples of heteroalkyl radicals included, but are not limited to, —CH2-CH2-O—CH3, —CH2-CH2-NH—CH3, —CH2-S—CH2-CH3, —CH2-CH2-S(O)—CH3, —CH2-CH2-S(O)2-CH3, —CH=CH—O—CH3, —CH2-CH=N—OCH3, —CH=CH—N(CH3)-CH3, —O—CH2-CH3 and others.

In the heteroalkyl radical, up to two or three heteroatoms may be consecutive placed, such as, for example, —CH2-NH—OCH3 y —CH2-O—Si(CH3)3. Note that the term "heteroalkyl" as used here in, include divalent aliphatic hydrocarbon radicals with a straight or branched chain consisting of at least one carbon atom and at least one heteroatom. Examples of divalent heteroalkyl included, but are not limited to, —CH2-CH2-S—CH2-CH2- and —CH2-S—CH2-CH2-NH—CH2-.

The terms "cycloalkyl" and "heterocycloalkyl", by themselves or in combination with other terms, refers to derived alicyclic hydrocarbon radicals, having one or more fused rings or covalently linked rings, rings that may be saturated, mono or polyunsaturated, where in the case of "cycloalkyl", the rings have only carbon and hydrogen atoms, while in the case of "heterocycloalkyl", the rings included at least one heteroatom from the following: O, N and S. Examples of monocyclic cycloalkyl include, but are not limited to, cyclopentyl, cyclohexyl, 1-cyclohexenyl, 2-cyclobutinyl, 1,3-cyclohexadienyl and others. Examples of cycloalkyl composed by several rings covalently linked include, but are not limited to, cyclobutylcyclopentyl and others. Examples of cycloalkyl formed by multiple fused rings, include the polycyclic compounds having two or more carbon atoms shared for two or more rings, for example bicycle-[4,2,0] octanyl, bicycle-[3,1,1]heptanyl, bicycle-[4,4,0]decanyl and others; and bicycle compounds with only one carbon atom shared by both rings, known as spirane for example, spiro-[3,4]octanyl.

Examples of heterocycloalkyl include, but are not limited to tetrahydrofuranyl, tetrahydropyranyl, dioxanyl, piperidinyl, morpholinyl, piperazinyl, pyrrolidinyl, thiolanyl and others. Note that the terms "cycloalkyl" and "heterocycloalkyl" include divalent alicyclic hydrocarbon radicals composed by one or more rings, fused or covalently linked, where such rings may be fully saturated, mono- or polyunsaturated, where in the case of cycloalkyl, rings are composed only by carbon and hydrogen atoms while in the case of heterocycloalkyl, at least one heteroatom is present.

The term "aryl" means an aromatic, polyunsaturated, hydrocarbon radical which can be a single ring (i.e. phenyl) or multiple rings (preferably from one to three rings) fused together (i.e., naftyl, antryl and others) or covalently linked (i.e. biphenyl).

The term "heteroaryl" refers to an aromatic hydrocarbon radical (preferably from one to three rings) containing at least one heteroatom from the following: N, O and S (in each single ring in the case of multiple rings). Examples of "aryl" and "heteroaryl" groups include, but do not limited to, 1-naftyl, 4-biphenyl, 1-pyrrolyl, 3-pyrazolyl, 2-imidazolyl, pyrazinyl, 2-oxazolyl, 2-thiazolyl, 3-furyl, 2-thienyl, 4-pyridyl, 2-benzothiazolyl, purinyl, 5-indolyl, 6-isoquinolyl and others. The terms "aryl" and "heteroaryl" include divalent radicals derived from an aromatic hydrocarbon, hydrocarbon composed only by carbon and hydrogen atoms, in the first case, and divalent radicals derived from aromatic hydrocarbon having one or more rings of carbon and hydrogen atoms with at least one heteroatom.

The term "arylalkyl" includes those radicals in which an aryl group is attached to one or more alkyl group (e.j., benzyl, phenyl, stirene and others). The term "heteroarylalkyl" refers to those radicals formed by one or more heteroalkyl groups attached to one or more aryl groups and/or those radicals formed by one or more heteroaryl groups attached to one or more alkyl groups (e.j., 2,5-dimethylfuran) and/or those radicals formed by one or more heteroaryl groups attached to one or more heteroalkyl groups.

The term "arylcycloalkyl" refers to those radicals formed by one or more aryl groups attached to one or more cycloalkyl groups (e.j., benzyl, phenyl, cumene, stirene, vinylbencene and others). The term "heteroarylcycloalkyl" refers to those radicals formed by one or more heteroaryl groups attached to one or more cycloalkyl groups, and/or those radicals formed by one or more heterocycloalkyl attached to one or more aryl groups and/or those radicals formed by one or more heterocycloalkyl groups attached to one or more heteroaryl groups.

The term "alkylcycloalkyl" refers to those radicals formed by one or more cycloalkyl rings substituted with one or more alkyl radicals. The term "heteroalkylcycloalkyl" refers to those radicals formed by one or more heteroalkyl group attached to one or more cycloalkyl rings, and/or those radicals formed by one or more heterocycloalkyl group substituted with one or more alkyl group and/or those radicals formed by one or more heterocycloalkyl groups substituted with one or more heteroalkyl groups.

The term "oxo" refers to an oxygen atom that is double bound to for example, any of the following atoms: carbon, nitrogen, sulfur and phosphorus. The term "halogen" refers to atoms of fluorine, chlorine, bromine and iodine. The term "heteroatom" refers to any atom other than carbon or hydrogen, usually oxygen, nitrogen, sulfur, phosphorus, boron, chlorine, bromine or iodine.

In the tables shown below appear, as examples, compounds which structure is represented by one of the formulas I to V. However, the compounds identified in the invention are not limited to the compounds summarized in Tables 1 to 5.

Table 1 shows examples of compounds represented by formula I of the invention.

TABLE 1

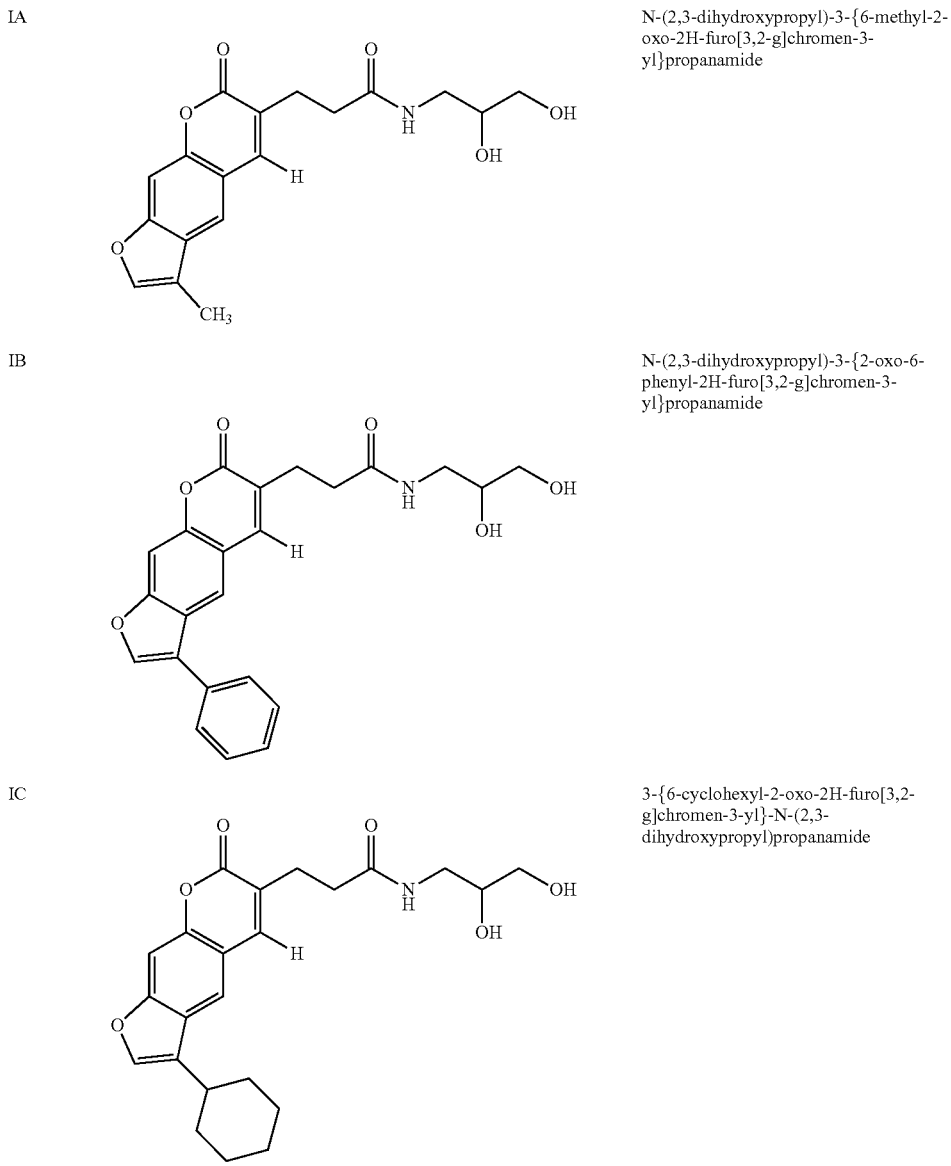

| | | |
|---|---|---|
| IA | | N-(2,3-dihydroxypropyl)-3-{6-methyl-2-oxo-2H-furo[3,2-g]chromen-3-yl}propanamide |
| IB | | N-(2,3-dihydroxypropyl)-3-{2-oxo-6-phenyl-2H-furo[3,2-g]chromen-3-yl}propanamide |
| IC | | 3-{6-cyclohexyl-2-oxo-2H-furo[3,2-g]chromen-3-yl}-N-(2,3-dihydroxypropyl)propanamide |

TABLE 1-continued

Chemical compounds represented by formula I.

| ID | | |
|---|---|---|
| ID | | 3-{6-cyclopentyl-2-oxo-2H-furo[3,2-g]chromen-3-yl}-N-(2,3-dihydroxypropyl)propanamide |
| IE | | N-(2,3-dihydroxypropyl)-3-[6-(naphthalen-2-yl)-2-oxo-2H-furo[3,2-g]chromen-3-yl]propanamide |
| IF | | N-(2,3-dihydroxypropyl)-3-{2-oxo-2H-furo[3,2-g]chromen-3-yl}propanamide |
| IG | | N-(2,3-dihydroxypropyl)-3-[2-oxo-6-(1H-pyrrol-1-yl)-2H-furo[3,2-g]chromen-3-yl]propanamide |
| IH | | N-(2,3-dihydroxypropyl)-3-{4,6-dimethyl-2-oxo-2H-furo[3,2-g]chromen-3-yl}propanamide |

TABLE 1-continued

Chemical compounds represented by formula I.

| | | |
|---|---|---|
| II | *(structure)* | N-(2,3-dihydroxypropyl)-3-{4-methyl-2-oxo-6-phenyl-2H-furo[3,2-g]chromen-3-yl}propanamide |
| IJ | *(structure)* | 3-{6-cyclohexyl-4-methyl-2-oxo-2H-furo[3,2-g]chromen-3-yl}-N-(2,3-dihydroxypropyl)propanamide |
| IK | *(structure)* | 3-{6-cyclopentyl-4-methyl-2-oxo-2H-furo[3,2-g]chromen-3-yl}-N-(2,3-dihydroxypropyl)propanamide |
| IL | *(structure)* | N-(2,3-dihydroxypropyl)-3-[4-methyl-6-(naphthalen-2-yl)-2-oxo-2H-furo[3,2-g]chromen-3-yl]propanamide |

TABLE 1-continued

Chemical compounds represented by formula I.

| | | |
|---|---|---|
| IM | | N-(2,3-dihydroxypropyl)-3-{4-methyl-2-oxo-2H-furo[3,2-g]chromen-3-yl}propanamide |
| IN | | N-(2,3-dihydroxypropyl)-3-[4-methyl-2-oxo-6-(1H-pyrrol-1-yl)-2H-furo[3,2-g]chromen-3-yl]propanamide |

Table 2 shows examples of compounds represented by formula II of the invention.

TABLE 2

Chemical compounds represented by formula II.

| | | |
|---|---|---|
| IIA | | N-(2,3-dihydroxypropyl)-2-{5-methyl-11-oxo-3,10-dioxatricyclo[7.4.0.0^{2,6}]trideca-1(9),4,7,12-tetraen-12-yl}acetamide |
| IIB | | N-(2,3-dihydroxypropyl)-2-{11-oxo-5-phenyl-3,10-dioxatricyclo[7.4.0.0^{2,6}]trideca-1(9),4,7,12-tetraen-12-yl}acetamide |
| IIC | | 2-{5-cyclohexyl-11-oxo-3,10-dioxatricyclo[7.4.0.0^{2,6}]trideca-1(9),4,7,12-tetraen-12-yl}-N-(2,3-dihydroxypropyl)acetamide |
| IID | | 2-{5-cyclopentyl-11-oxo-3,10-dioxatricyclo[7.4.0.0^{2,6}]trideca-1(9),4,7,12-tetraen-12-yl}-N-(2,3-dihydroxypropyl)acetamide |
| IIE | | N-(2,3-dihydroxypropyl)-2-[5-(naphthalen-2-yl)-11-oxo-3,10-dioxatricyclo[7.4.0.0^{2,6}]trideca-1(9),4,7,12-tetraen-12-yl]acetamide |

TABLE 2-continued

Chemical compounds represented by formula II.

| | | |
|---|---|---|
| IIF | | N-(2,3-dihydroxypropyl)-2-{11-oxo-3,10-dioxatricyclo[7.4.0.0^{2,6}]trideca-1(9),4,7,12-tetraen-12-yl}acetamide |
| IIG | | N-(2,3-dihydroxypropyl)-2-[11-oxo-5-(1H-pyrrol-1-yl)-3,10-dioxatricyclo[7.4.0.0^{2,6}]trideca-1(9),4,7,12-tetraen-12-yl]acetamide |
| IIH | | N-(2,3-dihydroxypropyl)-2-{5,13-dimethyl-11-oxo-3,10-dioxatricyclo[7.4.0.0^{2,6}]trideca-1(9),4,7,12-tetraen-12-yl}acetamide |
| III | | N-(2,3-dihydroxypropyl)-2-{13-methyl-11-oxo-5-phenyl-3,10-dioxatricyclo[7.4.0.0^{2,6}]trideca-1(9),4,7,12-tetraen-12-yl}acetamide |
| IIJ | | 2-{5-cyclohexyl-13-methyl-11-oxo-3,10-dioxatricyclo[7.4.0.0^{2,6}]trideca-1(9),4,7,12-tetraen-12-yl}-N-(2,3-dihydroxypropyl)acetamide |
| IIK | | 2-{5-cyclopentyl-13-methyl-11-oxo-3,10-dioxatricyclo[7.4.0.0^{2,6}]trideca-1(9),4,7,12-tetraen-12-yl}-N-(2,3-dihydroxypropyl)acetamide |
| IIL | | N-(2,3-dihydroxypropyl)-2-[13-methyl-5-(naphthalen-2-yl)-11-oxo-3,10-dioxatricyclo[7.4.0.0^{2,6}]trideca-1(9),4,7,12-tetraen-12-yl]acetamide |

TABLE 2-continued

Chemical compounds represented by formula II.

IIM

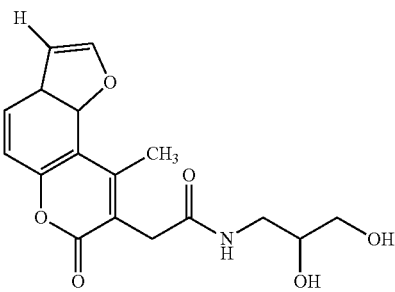 [SMILES: Cc1c2c(oc(=O)c1CC(=O)NCC(O)CO)C=CC1C=COC21]

N-(2,3-dihydroxypropyl)-2-{13-methyl-11-oxo-3,10-dioxatricyclo[7.4.0.0^{2,6}]trideca-1(9),4,7,12-tetraen-12-yl}acetamide

IIN

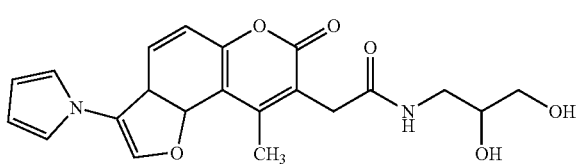 [SMILES: Cc1c2c(oc(=O)c1CC(=O)NCC(O)CO)C=CC1C(n3cccc3)=COC21]

N-(2,3-dihydroxypropyl)-2-[13-methyl-11-oxo-5-(1H-pyrrol-1-yl)-3,10-dioxatricyclo[7.4.0.0^{2,6}]trideca-1(9),4,7,12-tetraen-12-yl]acetamide Table 3 shows examples of compounds represented by formula III of the invention.

TABLE 3

Chemical compounds represented by formula III.

IIIA

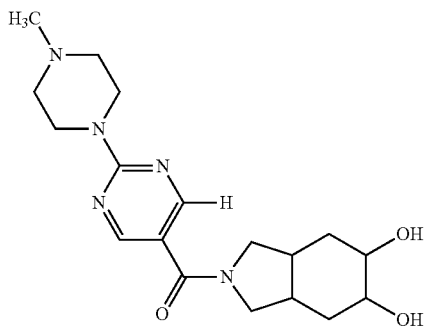 [SMILES: CN1CCN(c2ncc(C(=O)N3CC4CC(O)C(O)CC4C3)cn2)CC1]

2-{[2-(4-methylpiperazin-1-yl)pyrimidin-5-yl]carbonyl}-octahydro-1H-isoindole-5,6-diol

IIIB

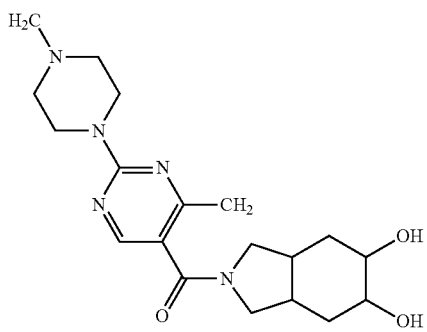 [SMILES: Cc1nc(N2CCN(C)CC2)ncc1C(=O)N1CC2CC(O)C(O)CC2C1]

2-{[4-methyl-2-(4-methylpiperazin-1-yl)pyrimidin-5-yl]carbonyl}-octahydro-1H-isoindole-5,6-diol TABLE 3-continued Chemical compounds represented by formula III.

| | | |
|---|---|---|
| IIIC | | 2-{[2-(4-phenylpiperazin-1-yl)pyrimidin-5-yl]carbonyl}-octahydro-1H-isoindole-5,6-diol |
| IIID | | 2-{[4-methyl-2-(4-phenylpiperazin-1-yl)pyrimidin-5-yl]carbonyl}-octahydro-1H-isoindole-5,6-diol |
| IIIE | | 2-{[2-(4-cyclohexylpiperazin-1-yl)pyrimidin-5-yl]carbonyl}-octahydro-1H-isoindole-5,6-diol |
| IIIF | | 2-{[2-(4-cyclohexylpiperazin-1-yl)-4-methylpyrimidin-5-yl]carbonyl}-octahydro-1H-isoindole-5,6-diol |

TABLE 3-continued

Chemical compounds represented by formula III.

IIIG 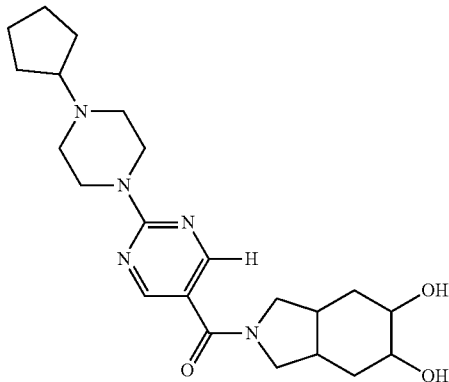 [SMILES: O=C(c1cnc(N2CCN(C3CCCC3)CC2)nc1)N1CC2CC(O)C(O)CC2C1] 2-{[2-(4-cyclopentylpiperazin-1-yl)pyrimidin-5-yl]carbonyl}-octahydro-1H-isoindole-5,6-diol IIIH 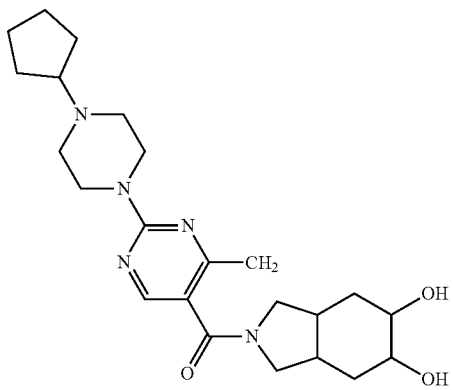 [SMILES: Cc1nc(N2CCN(C3CCCC3)CC2)ncc1C(=O)N1CC2CC(O)C(O)CC2C1] 2-{[2-(4-cyclopentylpiperazin-1-yl)-4-methylpyrimidin-5-yl]carbonyl)-octahydro-1H-isoindole-5,6-diol IIII 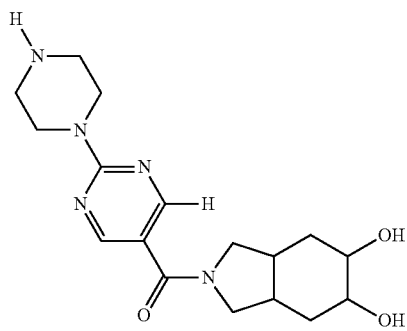 [SMILES: O=C(c1cnc(N2CCNCC2)nc1)N1CC2CC(O)C(O)CC2C1] 2-{[2-(piperazin-1-yl)pyrimidin-5-yl]carbonyl}-octahydro-1H-isoindole-5,6-diol IIIJ 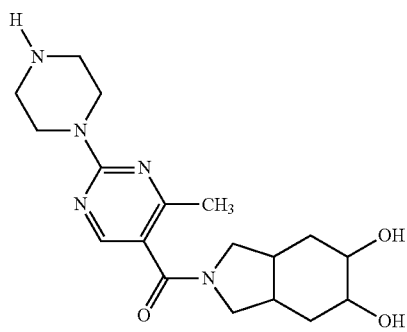 [SMILES: Cc1nc(N2CCNCC2)ncc1C(=O)N1CC2CC(O)C(O)CC2C1] 2-{[4-methyl-2-(piperazin-1-yl)pyrimidin-5-yl]carbonyl}-octahydro-1H-isoindole-5,6-diol TABLE 3-continued Chemical compounds represented by formula III.

| | | |
|---|---|---|
| IIIK | 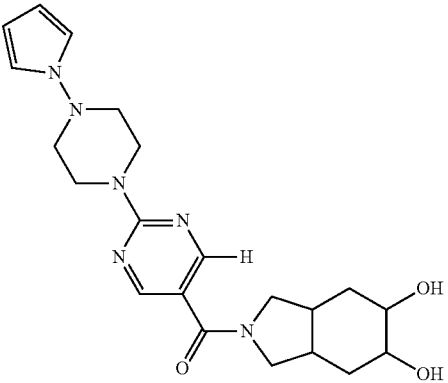 [SMILES: O=C(c1cnc(N2CCN(n3cccc3)CC2)nc1)N1CC2CC(O)C(O)CC2C1] | 2-({2-[4-(1H-pyrrol-1-yl)piperazin-1-yl]pyrimidin-5-yl}carbonyl)-octahydro-1H-isoindole-5,6-diol |
| IIIL | 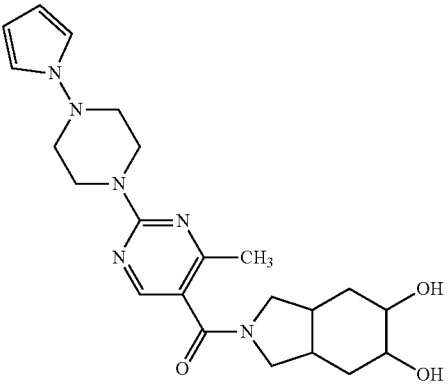 [SMILES: Cc1nc(N2CCN(n3cccc3)CC2)ncc1C(=O)N1CC2CC(O)C(O)CC2C1] | 2-({4-methyl-2-[4-(1H-pyrrol-1-yl)piperazin-1-yl]pyrimidin-5-yl}carbonyl)-octahydro-1H-isoindole-5,6-diol |

Table 4 shows examples of compounds represented by formula IV of the invention.

TABLE 4

Chemical compounds represented by formula IV.

| | | |
|---|---|---|
| IVA | 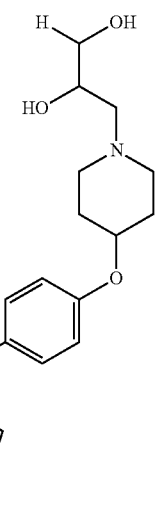 | 3-(4-{4-[(3-methylpyrrolidin-1-yl)carbonyl]phenoxy}piperidin-1-yl)propane-1,2-diol |

TABLE 4-continued
Chemical compounds represented by formula IV.
| | |
|---|---|
| IVB | 1-(4-{4-[(3-methylpyrrolidin-1-yl)carbonyl]phenoxy}piperidin-1-yl)butane-2,3-diol |
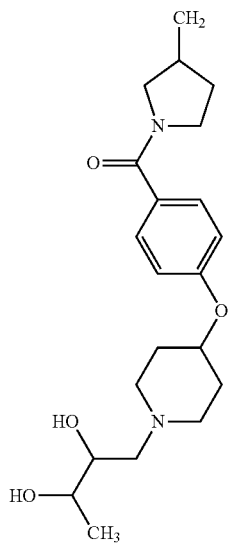 [SMILES: CC1CCN(C(=O)c2ccc(OC3CCN(CC(O)C(C)O)CC3)cc2)C1]
| | |
|---|---|
| IVC | 3-(4-{4-[(3-phenylpyrrolidin-1-yl)carbonyl]phenoxy}piperidin-1-yl)propane-1,2-diol |
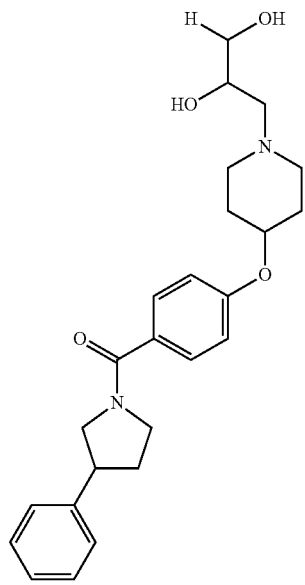 [SMILES: O=C(c1ccc(OC2CCN(CC(O)CO)CC2)cc1)N1CCC(c2ccccc2)C1]

TABLE 4-continued
Chemical compounds represented by formula IV.
| | |
|---|---|
| IVD | 1-(4-{4-[(3-phenylpyrrolidin-1-yl)carbonyl]phenoxy}piperidin-1-yl)butane-2,3-diol |
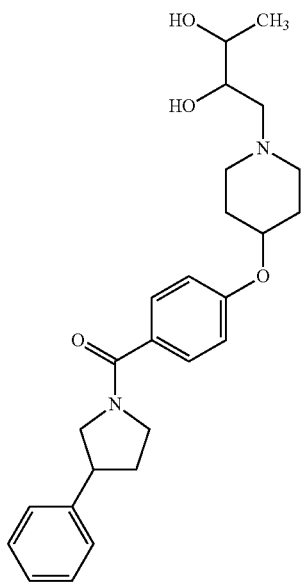 [SMILES: CC(O)C(O)CN1CCC(Oc2ccc(C(=O)N3CCC(c4ccccc4)C3)cc2)CC1]
| | |
|---|---|
| IVE | 3-(4-{4-[(3-[(3-yl)carbonyl]phenoxy}piperidin-1-yl)propane-1,2-diol |
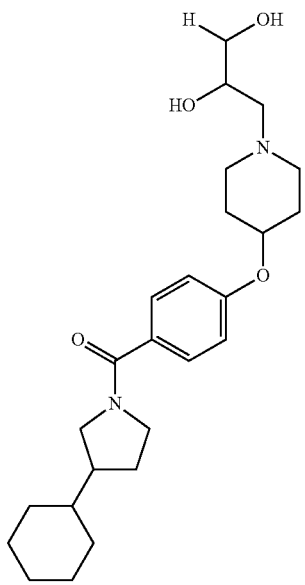 [SMILES: O=C(c1ccc(OC2CCN(CC(O)CO)CC2)cc1)N1CCC(C2CCCCC2)C1]

TABLE 4-continued
Chemical compounds represented by formula IV.
| IVF | 1-(4-{4-[(3-cyclohexylpyrrolidin-1-yl)carbonyl]phenoxy}piperidin-1-yl)butane-2,3-diol |
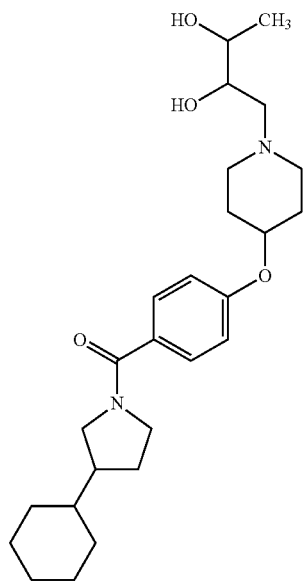 [SMILES: CC(O)C(O)CN1CCC(Oc2ccc(C(=O)N3CCC(C4CCCCC4)C3)cc2)CC1]
| IVG | 3-(4-{4-[(3-cyclopentylpyrrolidin-1-yl)carbonyl]phenoxy}piperidin-1-yl)propane-1,2-diol |
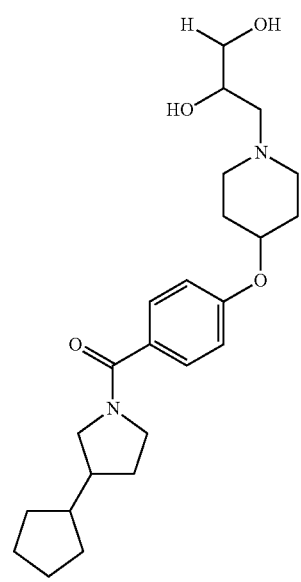 [SMILES: O=C(c1ccc(OC2CCN(CC(O)CO)CC2)cc1)N1CCC(C2CCCC2)C1]

TABLE 4-continued
Chemical compounds represented by formula IV.
| | |
|---|---|
| IVH | 1-(4-{4-[(3-cyclopentylpyrrolidin-1-yl)carbonyl]phenoxy}piperidin-1-yl)butane-2,3-diol |
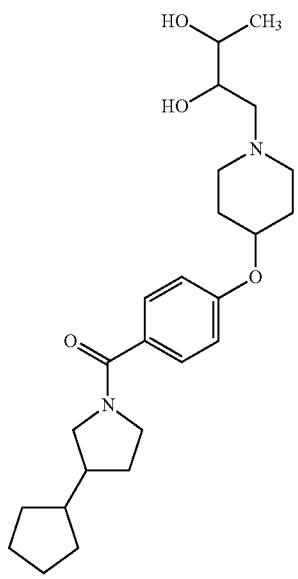 [SMILES: CC(O)C(O)CN1CCC(Oc2ccc(C(=O)N3CCC(C4CCCC4)C3)cc2)CC1]
| | |
|---|---|
| IVI | 3-(4-{4-[(pyrrolidin-1-yl)carbonyl]phenoxy}piperidin-1-yl)propane-1,2-diol |
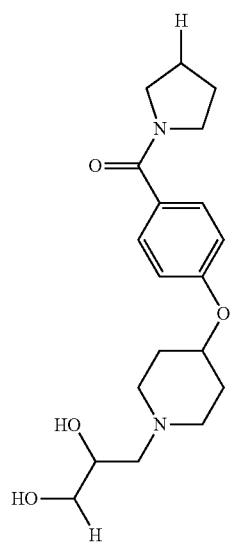 [SMILES: O=C(c1ccc(OC2CCN(CC(O)CO)CC2)cc1)N1CCCC1]

TABLE 4-continued
Chemical compounds represented by formula IV.
| | |
|---|---|
| IVJ | 1-(4-{4-[(pyrrolidin-1-yl)carbonyl]phenoxy}piperidin-1-yl)butane-2,3-diol |
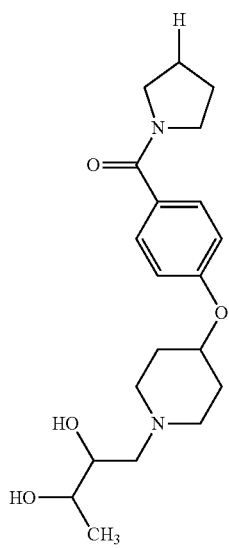 [SMILES: CC(O)C(O)CN1CCC(Oc2ccc(C(=O)N3CCCC3)cc2)CC1]
| | |
|---|---|
| IVK | 3-[4-(4-{[3-(1H-pyrrol-1-yl)pyrrolidin-1-yl]carbonyl}phenoxy)piperidin-1-yl]propane-1,2-diol |
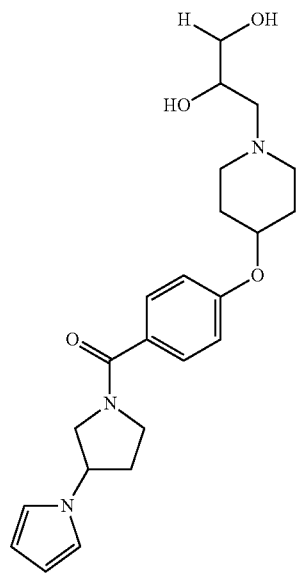 [SMILES: O=C(c1ccc(OC2CCN(CC(O)CO)CC2)cc1)N1CCC(n2cccc2)C1]

TABLE 4-continued

Chemical compounds represented by formula IV.

| | | |
|---|---|---|
| IVL | 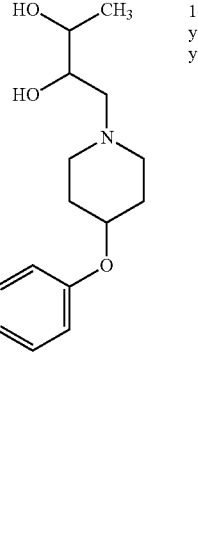 | 1-[4-(4-{[3-(1H-pyrrol-1-yl)pyrrolidin-1-yl]carbonyl}phenoxy)piperidin-1-yl]butane-2,3-diol |

Table 5 shows examples of compounds represented by formula V of the invention.

TABLE 5

Chemical compounds represented by formula V.

| | | |
|---|---|---|
| VA | 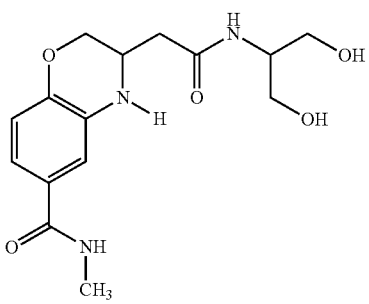 [SMILES: CNC(=O)c1ccc2c(c1)NC(CC(=O)NC(CO)CO)CO2] | 3-{[(1,3-dihydroxypropan-2-yl)carbamoyl]methyl}-N-methyl-3,4-dihydro-2H-1,4-benzoxazine-6-carboxamide |
| VB | 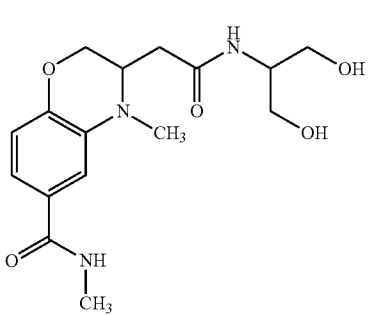 [SMILES: CNC(=O)c1ccc2c(c1)N(C)C(CC(=O)NC(CO)CO)CO2] | 3-{[(1,3-dihydroxypropan-2-yl)carbamoyl]methyl}-N,4-dimethyl-3,4-dihydro-2H-1,4-benzoxazine-6-carboxamide |

TABLE 5-continued

Chemical compounds represented by formula V.

| | | |
|---|---|---|
| VC | 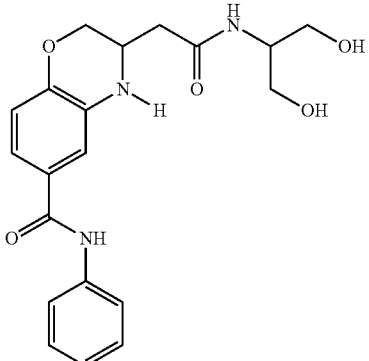 | 3-{[(1,3-dihydroxypropan-2-yl)carbamoyl]methyl}-N-phenyl-3,4-dihydro-2H-1,4-benzoxazine-6-carboxamide |
| VD | 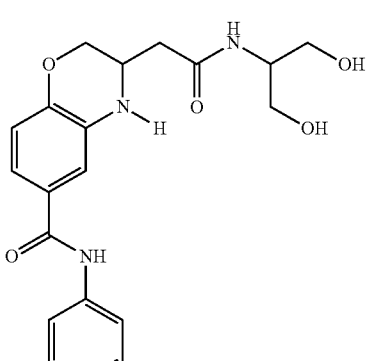 | 3-{[(1,3-dihydroxypropan-2-yl)carbamoyl]methyl}-4-methyl-N-phenyl-3,4-dihydro-2H-1,4-benzoxazine-6-carboxamide |
| VE | 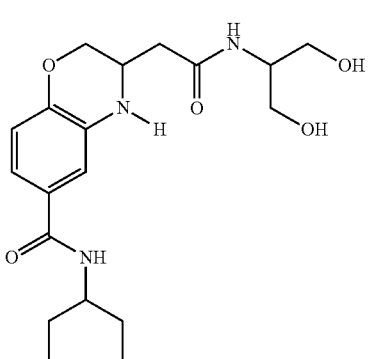 | N-cyclohexyl-3-{[(1,3-dihydroxypropan-2-yl)carbamoyl]methyl}-3,4-dihydro-2H-1,4-benzoxazine-6-carboxamide |
| VF | 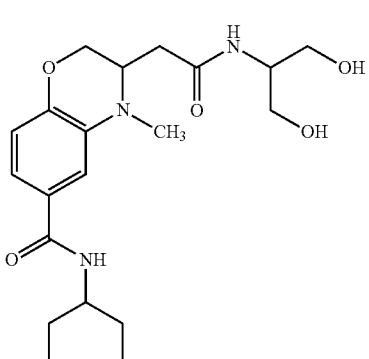 | N-cyclohexyl-3-{[(1,3-dihydroxypropan-2-yl)carbamoyl]methyl}-4-methyl-3,4-dihydro-2H-1,4-benzoxazine-6-carboxamide |

TABLE 5-continued

Chemical compounds represented by formula V.

| | | |
|---|---|---|
| VG | 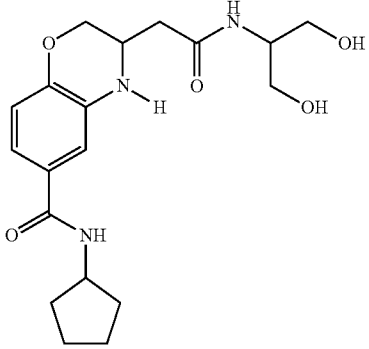 [SMILES: O=C(CC1COc2ccc(C(=O)NC3CCCC3)cc2N1)NC(CO)CO] | N-cyclopentyl-3-{[(1,3-dihydroxypropan-2-yl)carbamoyl]methyl}-3,4-dihydro-2H-1,4-benzoxazine-6-carboxamide |
| VH | 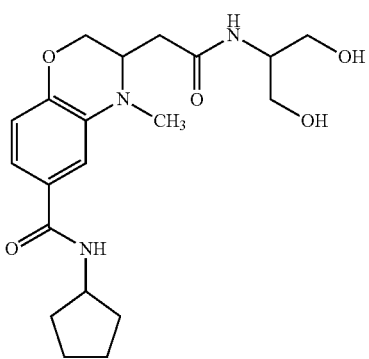 [SMILES: CN1c2cc(C(=O)NC3CCCC3)ccc2OCC1CC(=O)NC(CO)CO] | N-cyclopentyl-3-{[(1,3-dihydroxypropan-2-yl)carbamoyl]methyl}-4-methyl-3,4-dihydro-2H-1,4-benzoxazine-6-carboxamide |
| VI | 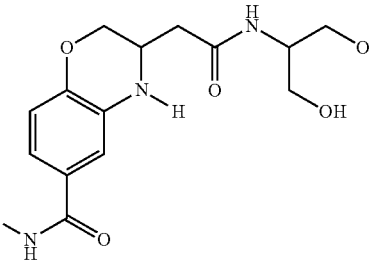 | 3-{[(1,3-dihydroxypropan-2-yl)carbamoyl]methyl}-3,4-dihydro-2H-1,4-benzoxazine-6-carboxamide |
| VJ | 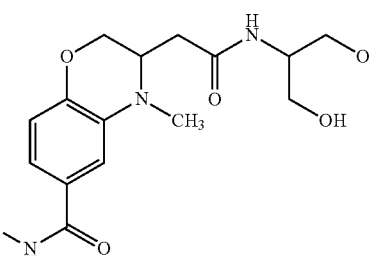 | 3-{[(1,3-dihydroxypropan-2-yl)carbamoyl]methyl}-4-methyl-3,4-dihydro-2H-1,4-benzoxazine-6-carboxamide |
| VK | 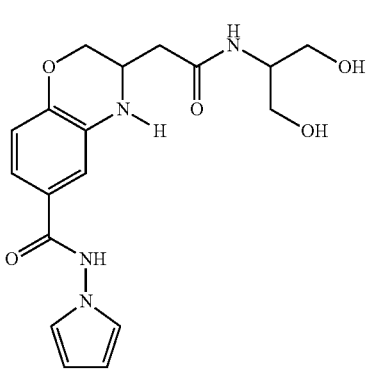 [SMILES: O=C(CC1COc2ccc(C(=O)Nn3cccc3)cc2N1)NC(CO)CO] | 3-{[(1,3-dihydroxypropan-2-yl)carbamoyl]methyl}-N-(1H-pyrrol-1-yl)-3,4-dihydro-2H-1,4-benzoxazine-6-carboxamide |

TABLE 5-continued

Chemical compounds represented by formula V.

VI 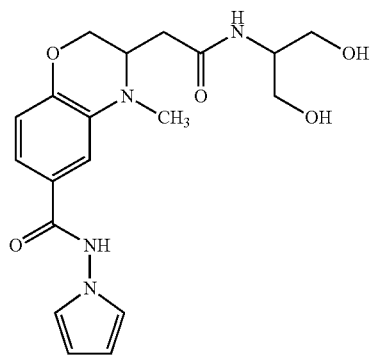 [SMILES: CN1c2cc(C(=O)Nn3cccc3)ccc2OCC1CC(=O)NC(CO)CO] 3-{[(1,3-dihydroxypropan-2-yl)carbamoyl]methyl}-4-methyl-N-(1H-pyrrol-1-yl)-3,4-dihydro-2H-1,4-benzoxazine-6-carboxamide In an embodiment of the invention, the disclosed method is used for the treatment of a disease caused by a phytopathogen, selected from the group composed by bacteria, oomycetes, fungi and nematodes. In a particular embodiment, the method is employed for the treatment of the Huanglongbing (HLB) disease, caused by the phytopathogen bacterium *Candidatus* 'Liberibacter asiaticus'.

As a materialization of the invention, in the disclosed method, the composition comprises between 0.01 µM and 5 µM of the compound of structure represented by one of the formulas I to V. In other materialization, said compound is applied to the plants once or twice a month.

A composition for agriculture that comprises at least one of the compounds of structure represented by one of the formulas I to V, or their salts, and an appropriate excipient or carrier is also an object of the invention.

In the invention, said compounds can be formulated as a suspension, solution, emulsion, powder, granule, emulsion concentrate, aerosol, impregnated granule, adjuvant, paste or through encapsulations. Said formulations are produced by known methods, for example, by mixing the active component with extenders, surfactants, emulsifiers and/or dispersers, and appropriate carriers.

In an embodiment of the invention, the active compound, that is at least one of the compounds with a formula selected from formula I up to formula V, is in the range from 0.01 µM to 5 µM in the composition. In a preferred embodiment, the composition is applied to the plants for the treatment of the disease caused by the bacterium *Candidatus* 'Liberibacter asiaticus', causal agent of the HLB disease.

Another object of the invention is the use of a compound with an structure represented by one of the formulas from I to V, or its salts, for the stimulation of the natural defense and the induction of resistance to plant diseases.

At present, the induction of disease resistance in plants is a method of great importance and interest, which allows the usage of biochemical and molecular mechanisms that already exist in the plant in the disease control. The plant defense to diseases comprises a series of events related to the recognition, signaling and response, defined as innate immunity of plants. This innate immunity can be activated by a number of factors, which decisively contribute to disease control. Among the possible defense mechanisms that are activated by the plant is the synthesis of antimicrobial compounds, like phytoalexins, defensins and pathogenesis-related proteins, among others. These responses are mediated by activation of genes related to salicylic acid, jasmonic acid/ethylene and hypersensitive response.

In the present invention, after the treatment with the compounds of formula selected from I to V, the activation of the GST1, PR1 y PDF 1.2 genes, which are markers of the salicylic acid, jasmonic acid/ethylene and hypersensitive response, is shown.

Hence, the invention also includes the use of the compounds that have the structure represented by one of the formulas I to V, or theft salts, for the manufacture of a composition for the preventive or curative treatment of the plant diseases. Prevention or treatment of said diseases is achieved through the activation of genes related to the route of the salicylic acid, jasmonic acid/ethylene and the hypersensitivity response. In an embodiment, the invention provides the preventive and curative treatment of plant diseases caused by bacteria, oomycetes, fungi and nematodes.

In a particular embodiment, the treatment with the compounds of structure represented by one of the formulas from I to V, in a range of concentration between 0.01-5 µM, allows the drastic reduction of the disease causative agents. It is achieved through the decrease in the number of the bacterium, oomycete, fungus or nematode copies, due to the treatment of the infected plants with the compounds disclosed in the invention. In a preferred embodiment, the phytopathogen is the bacterium *Candidatus* 'Liberibacter asiaticus'. In a more preferred embodiment, the compounds of structure represented by one of the formula from I to V are obtained by chemical synthesis.

DETAILED DESCRIPTION OF THE INVENTION/EXAMPLES

Example 1. Activation of Genes Related to the Natural Resistance of Plants to Disease after Treatment of Arabidopsis thaliana Plants with the Compounds of Formula I to V Arabidopsis plants were treated with the compounds at 1 µM. Leaves from ten plants were collected at 24 hours after spray application. Total RNA was extracted from leaves using the RNeasy kit (Qiagen, Valencia, Calif.) according to manufacturer's instructions, which includes a DNase treatment. The cDNAs were synthesized by using oligo-dT primer and reverse transcription kit SuperScript III (Invitrogen, Carlsbad, Calif.) according to manufacturer's instructions. The real-time quantitative PCR was performed using a RotorGene 3000 PCR machine (Corbett, Australia) and QuantiTect SYBR Green PCR kit (Qiagen). All sequences of primers for genes related to defense against diseases of Arabidopsis plants are shown in Table 6. The reaction conditions in real-time PCR were: an initial denaturation step at 95° C. for 15 min. followed by denaturation at 95° C. for 15 s, an alignment step for 30 s at 60° C. and an extension step for 30 s at 72° C. for 40 cycles. The analysis was carried out using the RotorGene 3000 software (Corbett, Australia) and five replicates were used for each sample. Experiments were repeated twice.

TABLE 6

Oligonucleotides used to detect genes related to the defense of diseases in plants of Arabidopsis thaliana.

| Arabidopsis thaliana genes analyzed | Oligonucleotides |
|---|---|
| PR-1 | GATGTGCCAAAGTGAGGTG TGCATGATCACATCATTACTTC |
| GST1 | TGGCTTCTGACCACTTCAC ACGCTCGTCGAAGAGTTTCT |
| PDF1.2 | TCATGGCTAAGTTTGCTTCC TGTCCCACTTGGCTTCTCGC |
| UBQ10 | CAGAACTTTGGCCGACTAC ATGGTCTTTCCGGTGAGAG |

Figure 1:
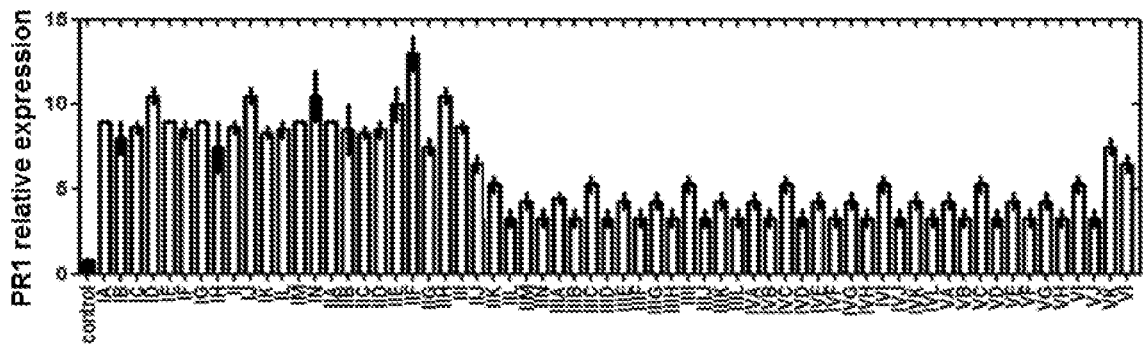
FIG. 1. Relative expression of genes related to defense responses to diseases in *Arabidopsis thaliana* plants treated with the compounds at the concentration of 1 µM. The bars represent the standard deviation of the mean, in 10 plants per each tested compound. The evaluated genes are related to the plant resistance, A: through the salicylic acid (PR1: pathogenesis related protein), B: jasmonic acid/ethylene (PDF 1.2: defensin) and C: the hypersensitivity response (GST1: glutathione S transferase).
Figure 1:
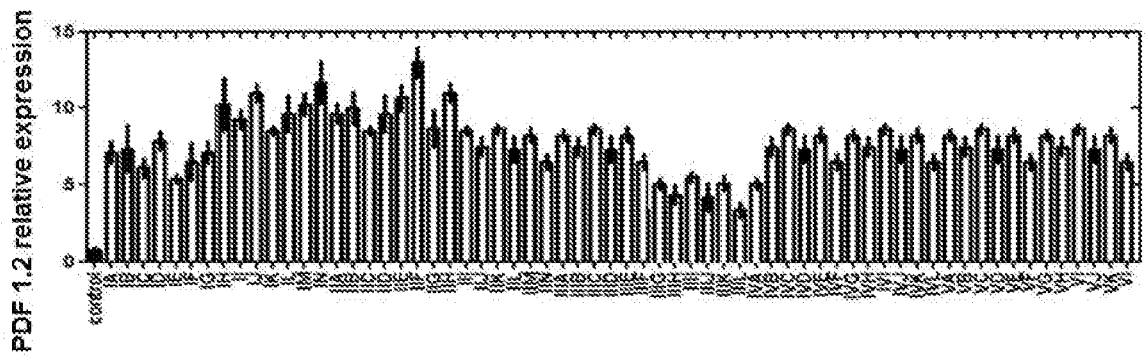
Figure 1:
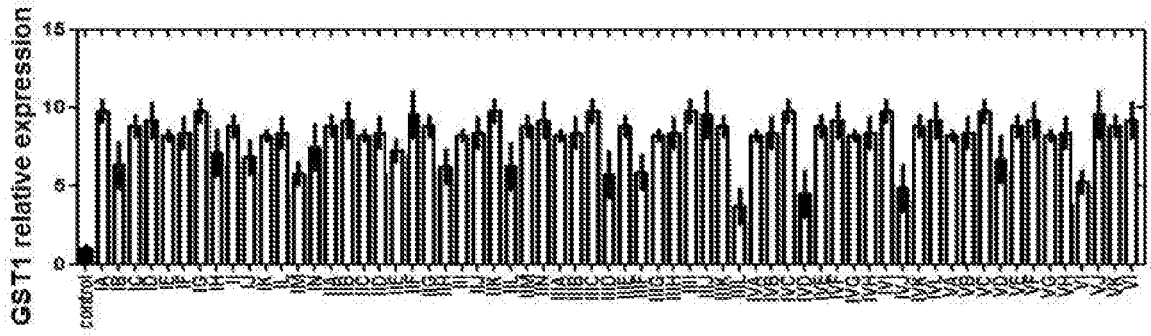

FIG. 1 shows as all analyzed genes were activated after treatment of Arabidopsis plants with the chemical compounds represented by the formula from I to V. The PR1, GST and PDF1.2 genes have an important role into innate immunity against plant diseases produced by fungus, bacterial and oomycete. Interesting, this behavior might predict the relation between its activation and biological activity.

Example 2. Activation of Genes Related to the Natural Plant Resistance to Diseases after the Treatment of Citrus Plants with Compounds of Formula I to V Citrus plants (Citrus sinensis) were treated with the compounds of formula I to V at 1 µM. Leaves from ten plants were collected at 24 hours after spray application. Total RNA was extracted from leaves using the RNeasy kit (Qiagen, Valencia, Calif.) according to manufacturer's instructions, which includes a DNase treatment. The cDNAs were synthesized by using oligo-dT primer and reverse transcription kit SuperScript III (Invitrogen, Carlsbad, Calif.) according to manufacturer's instructions. The real-time quantitative PCR was performed using a RotorGene 3000 PCR machine (Corbett, Australia) and QuantiTect SYBR Green PCR kit (Qiagen). All sequences of primers for genes related to defense against diseases of citrus plants are shown in Table 7. The reaction conditions in real-time PCR were: an initial denaturation step at 95° C. for 15 min. followed by denaturation at 95° C. for 15 s, an alignment step for 30 s at 60° C. and an extension step for 30 s at 72° C. for 40 cycles. The analysis was carried out using the RotorGene 3000 software (Corbett, Australia) and five replicates were used for each sample. Experiments were repeated twice.

TABLE 7

Oligonucleotides used to detect genes related to the defense against diseases in citrus plants.

| Citrus sinensis genes analyzed | Oligonucleotides |
|---|---|
| Phenylalanine ammonia-lyase (PAL) | AACGGGTTGCCTTCAAATCTTA ACATGATTGGTGACAGGATTGG |
| allene oxide synthase (AOS) | CCACACTTGGCTCGGATGC CGTGCGGAGCAATGGTTC |
| actin | GTGGCTCCACCAGAGAGAAA TGGATGGACCAGACTCATCA |

Figure 2:
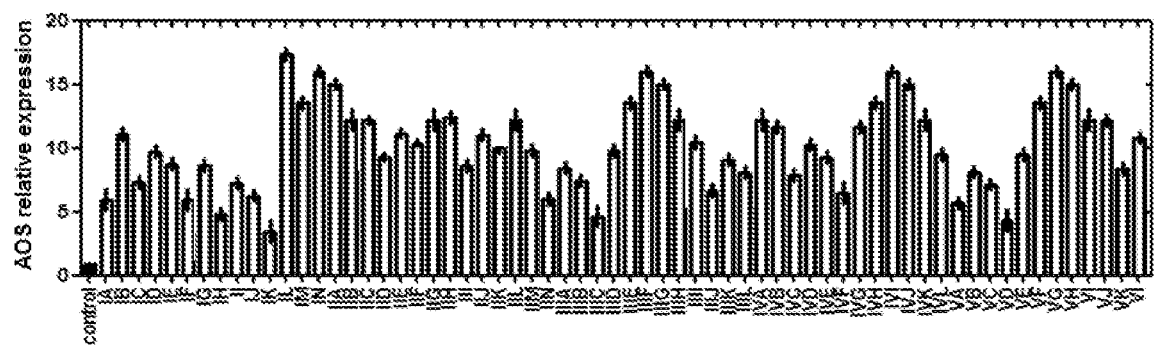
FIG. 2. Relative expression of genes related to defense responses to diseases in citrus plants treated with the compounds at the concentration of 1 µM. Bars represent the standard deviation of the mean of 10 plants per each tested compound. The tested genes are related to the resistance of plants through A: AOS: allene oxide synthase; B: PAL: phenylalanine-ammonia lyase.
Figure 2:
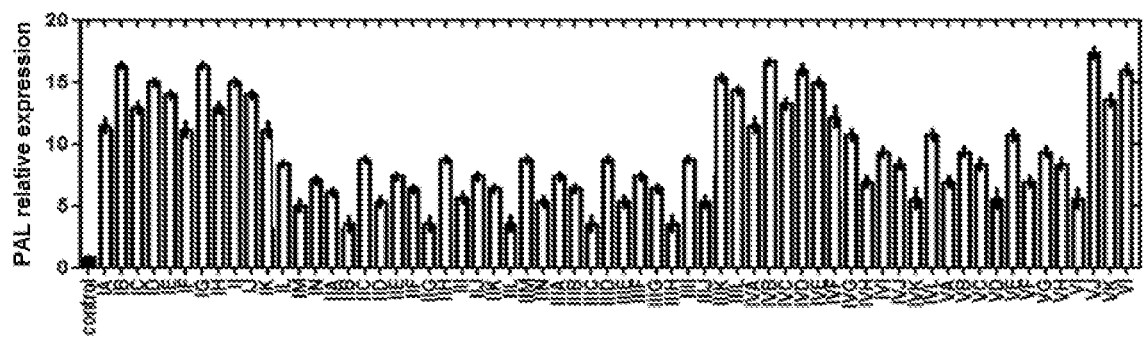

FIG. 2 shows as all analyzed genes (PAL and AOS) were activated after treatment of citrus plants with the molecules. The compounds identified in the invention were able to activate the defense in citrus plants like in Arabidopsis plants.

Example 3. Evaluation of the Effect of the Compounds of Formula I to V on the Control of the HLB Disease in Citrus The experiment was developed under greenhouses conditions. Plants with symptoms of HLB were placed in black plastic bags with a suitable irrigation regimen. The levels of the bacteria Candidatus 'Liberibacter asiaticus' in plants with symptoms of HLB were determined by real-time PCR, through the absolute quantification of bacteria in the leaves according to the standard curve and 16S ribosomal DNA amplified from the bacteria. Before the experiment, 10 plants per treatment were selected. Quantification of bacteria was done every 3 months, during a year. The last assessment was developed by taking all the leaves of the plant and performing a mixture prior to isolation of DNA. The concentration of the compounds of formula I to V was 1 µM and they were applied by spraying every 15 days. The DNA was extracted from leaves according to the protocol for isolation of DNA from Promega.

Figure 3:
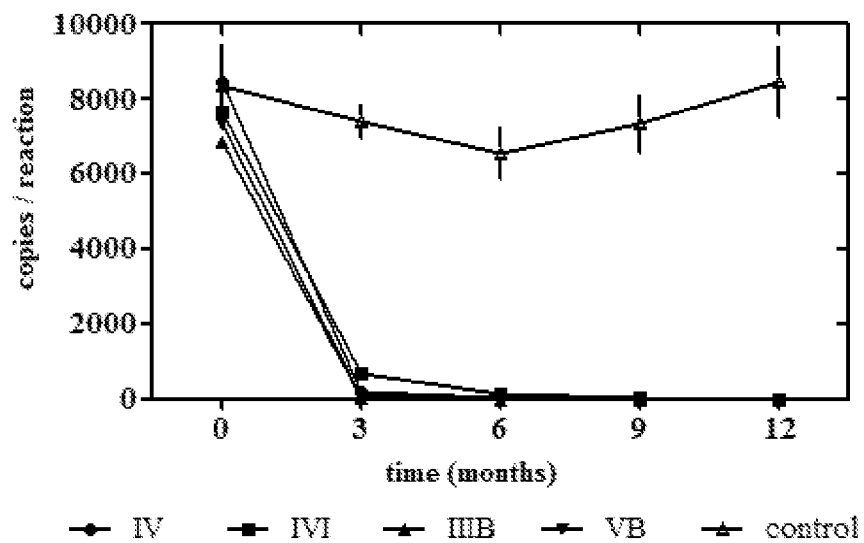
FIG. 3. Effect of the compounds, at the concentration of 1 µM, on the reduction of the titers of the pathogen bacterium causative of the HLB disease, in growing citrus plants. As a control, plants treated with water were used. Ten plants were used per each treatment. The bacterial titers were evaluated every 3 months, during a year.

The real-time quantitative PCR was performed using a RotorGene 3000 PCR machine (Corbett, Australia) and QuantiTect SYBR Green PCR kit (Qiagen). The oligonucleotides used for quantification of bacteria were: CTAATCCC-CAAAAGCCATCTC (SEQ ID NO: 15) and CTTCAGGCAAAACCAACTCC (SEQ ID NO: 16). The reaction conditions in real-time PCR were: an initial denaturation step at 95° C. for 15 min. followed by denaturation at 95° C. for 15 s, an alignment step for 30 s at 60° C. and an extension step for 30 s at 72° C. for 40 cycles. The analysis was carried out using the RotorGene 3000 software (Corbett, Australia) and five replicates were used for each sample. Experiments were repeated twice. As it can be seen, in the plants treated with compounds of formula I to V, a significant reduction in the levels of bacteria was obtained, reaching undetectable levels starting from month 4, and keeping said behaviour until the last evaluation, done at the end of the experiment (FIG. 3). As a control, sick plants treated with water, instead of the solution of the compounds, were employed. In said plants, the levels of the bacterium remained similar to those found at the beginning of the experiment, during all the evaluation time.

Example 4. Evaluation of Different Concentrations of Compounds of Formula I to V in the Control of the Citrus HLB Disease The objective of this experiment was to assess the minimum concentration of the compounds of formula I to V needed to control the citrus HLB disease. Ten growing citrus plants (*Citrus sinensis*) with HLB were used, per each dose. The concentrations tested were 0.001, 0.01, 0.1, 1, 5, and 10 µM, and the compounds were applied by spraying, every 15 days, for 12 months. The evaluation was performed 12 months after treatment. The levels of the bacteria *Candidatus* 'Liberibacter asiaticus' were determined as in Example 3. The average of the titers of bacterium in the plants was approximately 6000 copies per reaction. As it is shown in Table 8, from the concentrations of 0.01 to 5 µM of the assayed compounds, the bacterium levels were drastically reduced.

TABLE 8

Effect of different concentrations of the compounds on the bacterial causative agent of the HLB disease.

| Com-pound | Concentrations (µM) | | | | | |
|---|---|---|---|---|---|---|
| | 0 | 0.001 | 0.01 | 1 | 5 | 10 |
| IA | 5621* | 524 | 12 | 0 | 52 | 9652 |
| IB | 3214 | 598 | 15 | 0 | 98 | 9751 |
| IC | 8456 | 432 | 9 | 0 | 43 | 9632 |
| ID | 8745 | 123 | 0 | 0 | 123 | 5489 |
| IE | 9654 | 587 | 0 | 0 | 87 | 6574 |
| IF | 7895 | 985 | 0 | 0 | 98 | 6325 |
| IG | 3574 | 657 | 11 | 1 | 65 | 5423 |
| IH | 9523 | 658 | 8 | 12 | 68 | 4569 |
| II | 9541 | 756 | 14 | 14 | 76 | 8420 |
| IJ | 5632 | 456 | 0 | 18 | 46 | 5840 |
| IK | 5489 | 435 | 0 | 0 | 45 | 6521 |
| IL | 3658 | 578 | 0 | 0 | 78 | 3574 |
| IM | 8452 | 635 | 0 | 0 | 65 | 3541 |
| IN | 8632 | 524 | 0 | 0 | 54 | 2368 |
| IIA | 9652 | 598 | 14 | 0 | 98 | 9845 |

TABLE 8-continued

Effect of different concentrations of the compounds on the bacterial causative agent of the HLB disease.

| Com-pound | Concentrations (µM) | | | | | |
|---|---|---|---|---|---|---|
| | 0 | 0.001 | 0.01 | 1 | 5 | 10 |
| IIB | 9751 | 432 | 17 | 2 | 43 | 8654 |
| IIC | 9632 | 123 | 25 | 2 | 23 | 4562 |
| IID | 5489 | 587 | 12 | 2 | 87 | 1351 |
| IIE | 6574 | 985 | 1 | 5 | 98 | 2547 |
| IIF | 6325 | 657 | 9 | 0 | 67 | 6547 |
| IIG | 5423 | 658 | 0 | 3 | 68 | 4587 |
| IIH | 4569 | 756 | 0 | 1 | 76 | 2365 |
| III | 8420 | 456 | 0 | 1 | 56 | 3654 |
| IIJ | 5840 | 435 | 1 | 1 | 45 | 6541 |
| IIK | 6521 | 578 | 8 | 0 | 78 | 2365 |
| IIL | 3574 | 635 | 1 | 0 | 65 | 5478 |
| IIM | 3541 | 524 | 0 | 0 | 54 | 8542 |
| IIN | 2368 | 598 | 0 | 0 | 98 | 9654 |
| IIIA | 9845 | 432 | 0 | 0 | 43 | 2365 |
| IIIB | 8654 | 123 | 0 | 0 | 23 | 8546 |
| IIIC | 4562 | 587 | 0 | 0 | 87 | 3654 |
| IIID | 1351 | 985 | 1 | 0 | 98 | 9653 |
| IIIE | 2547 | 657 | 7 | 0 | 67 | 8653 |
| IIIF | 9547 | 658 | 5 | 4 | 68 | 3654 |
| IIIG | 8542 | 756 | 12 | 5 | 76 | 9654 |
| IIIH | 9853 | 456 | 15 | 6 | 56 | 3657 |
| IIII | 5478 | 435 | 9 | 8 | 45 | 8654 |
| IIIJ | 9854 | 578 | 0 | 7 | 578 | 7546 |
| IIIK | 6524 | 635 | 0 | 3 | 65 | 8420 |
| IIIL | 6547 | 524 | 0 | 6 | 54 | 5840 |
| IVA | 4587 | 598 | 1 | 5 | 98 | 6521 |
| IVB | 2365 | 432 | 8 | 4 | 43 | 3574 |
| IVC | 3654 | 123 | 4 | 0 | 23 | 3541 |
| IVD | 6541 | 587 | 0 | 0 | 87 | 2368 |
| IVE | 2365 | 985 | 0 | 0 | 98 | 9845 |
| IVF | 5478 | 657 | 0 | 0 | 67 | 8654 |
| IVG | 8542 | 658 | 0 | 0 | 68 | 4562 |
| IVH | 9654 | 756 | 0 | 0 | 76 | 1351 |
| IVI | 2365 | 456 | 4 | 2 | 56 | 2547 |
| IVJ | 8546 | 435 | 7 | 3 | 45 | 9547 |
| IVK | 3654 | 578 | 5 | 4 | 78 | 8542 |
| IVL | 9653 | 635 | 1 | 7 | 65 | 9853 |
| VA | 8653 | 524 | 1 | 5 | 54 | 5478 |
| VB | 3654 | 598 | 9 | 2 | 98 | 9854 |
| VC | 9654 | 432 | 0 | 4 | 43 | 6524 |
| VD | 3657 | 123 | 0 | 0 | 23 | 6547 |
| VE | 8654 | 587 | 0 | 0 | 87 | 4587 |
| VF | 7546 | 985 | 1 | 0 | 98 | 2365 |
| VG | 6548 | 657 | 8 | 0 | 67 | 3654 |
| VH | 6325 | 658 | 4 | 0 | 68 | 6541 |
| VI | 8456 | 756 | 0 | 0 | 76 | 4562 |
| VJ | 3654 | 456 | 0 | 0 | 56 | 1351 |
| VK | 8456 | 435 | 0 | 0 | 45 | 2547 |
| VI | 7777 | 578 | 0 | 0 | 78 | 9547 |

*Titers of the bacterium (12 months after the treatment with the compounds, at the indicated concentration)

Figure 4:
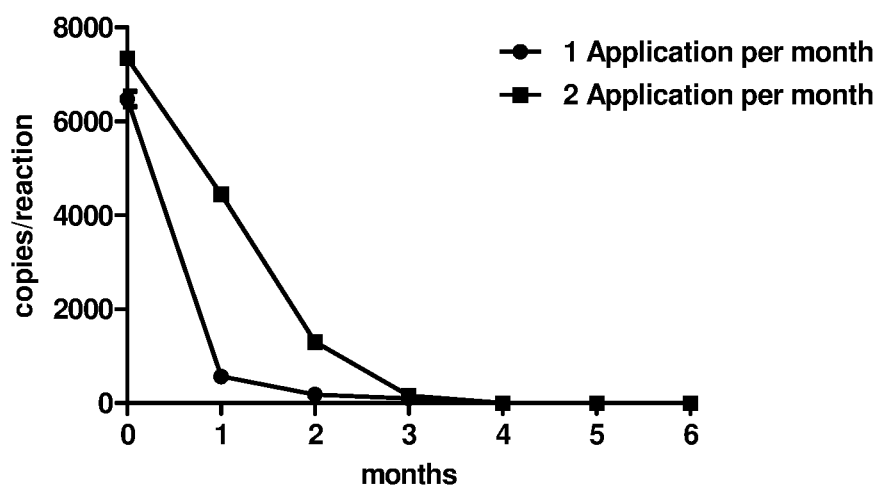
FIG. 4. Effect of the frequency of application of the compounds on the reduction of the titers of the bacterial causative agent of the HLB disease. The compound was applied at the concentration of 1 µM. The bacterial titers were evaluated during 6 months.

Example 5. Evaluation of the Effect of Application Frequency of the Compounds on the Control of the Citrus HLB Disease The objective of this experiment was to determine the influence of frequency of spray application of the compound IB on the control of citrus HLB disease in diseased citrus plants. Ten plants were used per treatment, and the studied application frequencies were: once and twice a month, during 6 months. The concentration used was 1 µM and the determinations of the bacterium level were performed every month. The levels of the bacteria *Candidatus* 'Liberibacter asiaticus' were determined as in Example 3. As it can be seen in FIG. 4, the bacterial reduction was observed in both tested variants. The application once a month reduced significantly the levels of the bacterium, compared to the application twice a month.

Example 6. Evaluation of the Effect of the Compounds of Formula I to V on the Control of Other Plant Diseases In order to compare the effect of the compounds of formula I to V on the control of diseases in different plants, experiments were conducted in tobacco, tomato and *Arabidopsis thaliana* plants inoculated with *Phytophthora parasitica*, *Rhizoctonia solani*, *Alternaria solani*, *Nocardia* sp and *Botrytis cinerea*, respectively. The compounds were applied by spraying, at a concentration of 1 µM, every 24 hours for one week. The plant mortality rate was determined for the disease produced by *Phytophthora parasitica*, *Rhizoctonia solani* and *Nocardia* sp, while the percentage of leaves with symptoms was determined for the infection by *Alternaria solani*. In the case of plants affected by *Botrytis cinerea*, the lesion diameter was measured. Table 9 shows that the compounds had a marked effect in the reduction of the mortality due to several plant diseases, a decrease in the symptoms caused by them was also observed. Each treatment included fifty plants. As control, plants treated with water were studied. The plants of each treatment were previously inoculated with the indicated pathogens, according to different inoculation protocols (*Frontiers in Plant Science* 3: 268, 1-6, 2012), and later they were treated with the compounds.

TABLE 9

Effect of the assayed compounds on the control of different plant diseases produced by fungi, oomycetes and bacteria.

| Com- pound control | Pathogen | | | | | | | |
|---|---|---|---|---|---|---|---|---|
| | Pp-Nt 91 * | Rs-Nt 87 * | N-Nt 58 * | Rs-SI 96 * | As-SI 68 ** | Bc-At 8.7 *** | Bc-Nt 6.7 *** | Bc-SI 7.4 *** |
| IA  | 1 | 2 | 1 | 3 | 1 | 1.2 | 0.3 | 0.8 |
| IB  | 2 | 3 | 1 | 2 | 2 | 1.1 | 2.0 | 1.6 |
| IC  | 1 | 4 | 2 | 2 | 3 | 0.5 | 0.9 | 0.8 |
| ID  | 0 | 0 | 1 | 2 | 8 | 1.5 | 1.5 | 2.5 |
| IE  | 0 | 0 | 0 | 0 | 7 | 2.4 | 1.5 | 0.8 |
| IF  | 0 | 0 | 0 | 1 | 5 | 0.7 | 0.9 | 1.2 |
| IG  | 3 | 0 | 0 | 1 | 7 | 1.2 | 0.3 | 0.8 |
| IH  | 1 | 2 | 1 | 3 | 1 | 1.1 | 2.0 | 1.6 |
| II  | 2 | 3 | 1 | 2 | 2 | 0.5 | 0.9 | 0.8 |
| IJ  | 1 | 4 | 2 | 2 | 3 | 1.5 | 1.5 | 2.5 |
| IK  | 0 | 0 | 1 | 2 | 8 | 2.4 | 1.5 | 0.8 |
| IL  | 0 | 0 | 0 | 0 | 7 | 0.7 | 0.9 | 1.2 |
| IM  | 0 | 0 | 0 | 1 | 5 | 1.2 | 0.3 | 0.8 |
| IN  | 3 | 0 | 0 | 1 | 7 | 1.1 | 2.0 | 1.6 |
| IIA | 1 | 2 | 1 | 3 | 1 | 0.5 | 0.9 | 0.8 |
| IIB | 2 | 3 | 1 | 2 | 2 | 1.5 | 1.5 | 2.5 |
| IIC | 1 | 4 | 2 | 2 | 3 | 2.4 | 1.5 | 0.8 |
| IID | 0 | 0 | 1 | 2 | 8 | 0.7 | 0.9 | 1.2 |
| IIE | 0 | 0 | 0 | 0 | 7 | 1.2 | 0.3 | 0.8 |
| IIF | 0 | 0 | 0 | 1 | 5 | 1.1 | 2.0 | 1.6 |
| IIG | 3 | 0 | 0 | 1 | 7 | 0.5 | 0.9 | 0.8 |
| IIH | 1 | 2 | 1 | 3 | 1 | 1.5 | 1.5 | 2.5 |
| III | 2 | 3 | 1 | 2 | 2 | 2.4 | 1.5 | 0.8 |
| IIJ | 1 | 4 | 2 | 2 | 3 | 0.7 | 0.9 | 1.2 |
| IIK | 0 | 0 | 1 | 2 | 8 | 1.2 | 0.3 | 0.8 |
| IIL | 0 | 0 | 0 | 0 | 7 | 1.1 | 2.0 | 1.6 |
| IIM | 0 | 0 | 0 | 1 | 5 | 0.5 | 0.9 | 0.8 |
| IIN | 3 | 0 | 0 | 1 | 7 | 1.5 | 1.5 | 2.5 |
| IIIA | 1 | 2 | 1 | 3 | 1 | 2.4 | 1.5 | 0.8 |
| IIIB | 2 | 3 | 1 | 2 | 2 | 0.7 | 0.9 | 1.2 |
| IIIC | 1 | 4 | 2 | 2 | 3 | 1.2 | 0.3 | 0.8 |
| IIID | 0 | 0 | 1 | 2 | 8 | 1.1 | 2.0 | 1.6 |
| IIIE | 0 | 0 | 0 | 0 | 7 | 0.5 | 0.9 | 0.8 |
| IIIF | 0 | 0 | 0 | 1 | 5 | 1.5 | 1.5 | 2.5 |
| IIIG | 3 | 0 | 0 | 1 | 7 | 2.4 | 1.5 | 0.8 |
| IIIH | 1 | 2 | 1 | 3 | 1 | 0.7 | 0.9 | 1.2 |
| IIII | 2 | 3 | 1 | 2 | 2 | 1.2 | 0.3 | 0.8 |
| IIIJ | 1 | 4 | 2 | 2 | 3 | 1.1 | 2.0 | 1.6 |
| IIIK | 0 | 0 | 1 | 2 | 8 | 0.5 | 0.9 | 0.8 |
| IIIL | 0 | 0 | 0 | 0 | 7 | 1.5 | 1.5 | 2.5 |
| IVA | 0 | 0 | 0 | 1 | 5 | 2.4 | 1.5 | 0.8 |
| IVB | 3 | 0 | 0 | 1 | 7 | 0.7 | 0.9 | 1.2 |
| IVC | 1 | 2 | 1 | 3 | 1 | 1.2 | 0.3 | 0.8 |
| IVD | 2 | 3 | 1 | 2 | 2 | 1.1 | 2.0 | 1.6 |
| IVE | 1 | 4 | 2 | 2 | 3 | 0.5 | 0.9 | 0.8 |
| IVF | 0 | 0 | 1 | 2 | 8 | 1.5 | 1.5 | 2.5 |
| IVG | 0 | 0 | 0 | 0 | 7 | 2.4 | 1.5 | 0.8 |
| IVH | 0 | 0 | 0 | 1 | 5 | 0.7 | 0.9 | 1.2 |
| IVI | 3 | 0 | 0 | 1 | 7 | 1.2 | 0.3 | 0.8 |
| IVJ | 1 | 2 | 1 | 3 | 1 | 1.1 | 2.0 | 1.6 |
| IVK | 1 | 2 | 1 | 3 | 1 | 0.5 | 0.9 | 0.8 |
| IVL | 2 | 3 | 1 | 2 | 2 | 1.5 | 1.5 | 2.5 |
| VA  | 1 | 4 | 2 | 2 | 3 | 2.4 | 1.5 | 0.8 |
| VB  | 0 | 0 | 1 | 2 | 8 | 0.7 | 0.9 | 1.2 |
| VC  | 0 | 0 | 0 | 0 | 7 | 1.2 | 0.3 | 0.8 |
| VD  | 0 | 0 | 0 | 1 | 5 | 1.1 | 2.0 | 1.6 |
| VE  | 3 | 0 | 0 | 1 | 7 | 0.5 | 0.9 | 0.8 |
| VF  | 1 | 2 | 1 | 3 | 1 | 1.5 | 1.5 | 2.5 |
| VG  | 1 | 2 | 1 | 3 | 1 | 2.4 | 1.5 | 0.8 |
| VH  | 2 | 3 | 1 | 2 | 2 | 0.7 | 0.9 | 1.2 |
| VI  | 1 | 4 | 2 | 2 | 3 | 0.7 | 0.9 | 1.2 |
| VJ  | 0 | 0 | 1 | 2 | 8 | 1.2 | 0.3 | 0.8 |
| VK  | 0 | 0 | 0 | 0 | 7 | 1.1 | 2.0 | 1.6 |
| VI  | 0 | 0 | 0 | 1 | 5 | 0.5 | 0.9 | 0.8 |

Pp-Nt: *Phytophthora parasitica*-tobacco;
Rs-Nt: *Rhizoctonia solani*-tobacco;
N-Nt: *Nocardia* sp-tobacco;
Rs-SI: *Rhizoctonia solani*-tomato;
As-SI: *Alternaria solani*-tomato;
Bc-At: *Botrytis cinerea*-*Arabidopsis*;
Bc-Nt: *Botrytis cinerea*-tobacco;
Bc-SI: *Botrytis cinerea*-tomato.

* The values represent the percentage (%) of mortality due to said disease.
** The values represent the percentage (%) of leaves with the disease symptoms.
*** The values represent the mean of the diameter (mm) of the lesion produced by the disease.

Example 7. Evaluation of the Protective Effect of the Compounds of Formula I to V on the HLB Citrus Disease This experiment was developed to determine the protective effect of the application of the compounds, once a month, at a concentration of 1 µM, on citrus plants without HLB symptoms, in an area with citrus plants affected by HLB and high levels of insect vector population. Ten citrus plants free from HLB were studied per treatment, and they received a solution of the compound to be evaluated, by spray; and citrus plants free from HLB were not treated with the compounds. The levels of the *Candidatus* 'Liberibacter asiaticus' bacterium were determined as in Example 3. The treatment of citrus plants free from HLB with the compounds of formula I to V allowed the protection of said plants from the bacterial infection through the vector. In said treated plants, the titers of the bacterium remain very low, between 1 and 4, while in the untreated plants, that did not receive the compounds; the levels of bacteria were increasing as the months passed. At the beginning of the experiment, the titers of the bacterium in the untreated plants were 5621, while one year later the average titer increased up to 6584. In said control plants, untreated with the compounds, two years later the bacterial titers continued increasing up to 8456. The symptoms of the HLB disease also were up in the control plants that remain untreated. The result achieved after the application of the compounds of formula I to V was unexpected, and allows the use of compositions that comprise said compounds, for the protection of citrus against said significant disease.

Example 8. Evaluation of the Protective Effect of the Compounds of Formula I to V on the Damages Caused by Nematodes The solutions of the compounds were prepared in ethanol and diluted in water, up to a concentration of 1 μM for a foliar application. Applications were conducted every 5 days, spraying only the leafs with each compound. Ten plants were used for each treatment and the final evaluation was performed 35 days after, by quantifying the number of nodules per plant. As shown in Table 10, the compounds induced a systemic effect on nematodes, with a significant reduction in the number of nodules per plant, in the studied crops. By this way, the effectiveness of the compounds in controlling high populations of the plant parasitic nematodes *Meloidogyne incognita*, *Radopholus similis* and *Pratylenchus coffeae* in tomato, banana and plantain was demonstrated.

TABLE 10

Effect of the compounds of formula I to V in the nematode control.

| Compound | Nematode | | |
|---|---|---|---|
| | Rs | Mi | Pc |
| control | 45 | 34 | 42 |
| IA | 12 | 23 | 18 |
| IB | 24 | 3 | 13 |
| IC | 13 | 4 | 22 |
| ID | 0 | 0 | 11 |
| IE | 0 | 0 | 0 |
| IF | 0 | 0 | 0 |
| IG | 31 | 0 | 0 |
| IH | 19 | 21 | 11 |
| II | 2 | 3 | 13 |
| IJ | 18 | 4 | 24 |
| IK | 0 | 0 | 15 |
| IL | 0 | 0 | 0 |
| IM | 0 | 0 | 0 |
| IN | 3 | 0 | 0 |
| IIA | 17 | 2 | 14 |
| IIB | 2 | 3 | 14 |
| IIC | 18 | 4 | 2 |
| IID | 0 | 0 | 17 |
| IIE | 0 | 0 | 0 |
| IIF | 0 | 0 | 0 |
| IIG | 3 | 0 | 0 |
| IIH | 16 | 2 | 18 |
| III | 2 | 3 | 1 |
| IIJ | 12 | 4 | 2 |
| IIK | 0 | 0 | 14 |
| IIL | 0 | 0 | 0 |
| IIM | 0 | 0 | 0 |
| IIN | 3 | 0 | 0 |
| IIIA | 11 | 2 | 16 |
| IIIB | 2 | 3 | 16 |
| IIIC | 14 | 4 | 2 |
| IIID | 0 | 0 | 18 |
| IIIE | 0 | 0 | 0 |
| IIIF | 0 | 0 | 0 |
| IIIG | 3 | 0 | 0 |
| IIIH | 14 | 2 | 16 |
| IIII | 2 | 3 | 12 |
| IIIJ | 12 | 4 | 2 |
| IIIK | 0 | 0 | 14 |
| IIIL | 0 | 0 | 0 |
| IVA | 0 | 0 | 0 |
| IVB | 3 | 0 | 0 |
| IVC | 14 | 2 | 13 |
| IVD | 2 | 3 | 15 |
| IVE | 14 | 4 | 2 |
| IVF | 0 | 0 | 17 |
| IVG | 0 | 0 | 0 |
| IVH | 0 | 0 | 0 |
| IVI | 3 | 0 | 0 |
| IVJ | 16 | 2 | 18 |
| IVK | 14 | 2 | 14 |
| IVL | 2 | 3 | 12 |
| VA | 1 | 4 | 2 |
| VB | 0 | 0 | 1 |
| VC | 0 | 0 | 0 |
| VD | 0 | 0 | 0 |
| VE | 3 | 0 | 0 |
| VF | 1 | 2 | 1 |
| VG | 1 | 2 | 1 |
| VH | 2 | 3 | 1 |
| VI | 1 | 4 | 2 |
| VJ | 0 | 0 | 14 |
| VK | 0 | 0 | 0 |
| VI | 0 | 0 | 0 |

Rs: *Radopholus similis*;
Mi: *Meloidogyne incognita*;
Pc: *Pratylenchus coffeae*.
* The values represent the number of nodules per plant.

INCORPORATION OF SEQUENCE LISTING

A Sequence Listing conforming to the rules of WIPO Standard ST.25 is hereby incorporated by reference. The Sequence Listing has been filed as an electronic document via EFS-Web in ASCII format. The electronic document, created on Jun. 4, 2020, is entitled "Corrected_Sequence_Listing 976-97_PCTUSCON.txt", and is 4,055 bytes in size.

The invention claimed is:

1. A method for the treatment of plant diseases comprising application to the plants of an effective amount of a composition comprising at least one compound of formula III or its salts, (III)

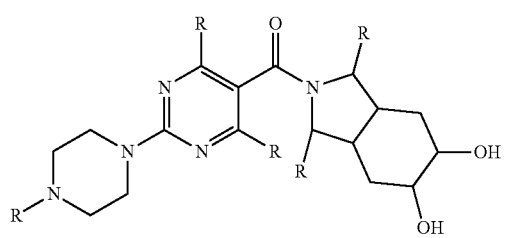

wherein:

R is selected from the group consisting of hydrogen, hydroxyl, halogen, alkyl $C_{1-12}$, heteroalkyl $C_{1-12}$, cycloalkyl $C_{3-7}$, heterocycloalkyl $C_{3-7}$, aryl, heteroaryl, arylalkyl $C_{1-3}$, heteroarylalkyl $C_{1-3}$, arylcycloalkyl $C_{1-7}$, heteroarylcycloalkyl $C_{1-7}$, alkyl $C_{1-3}$cycloalkyl $C_{3-7}$, and heteroalkyl $C_{1-3}$ cycloalkyl $C_{3-7}$;

wherein the plant disease is caused by a phytopathogen selected from the group consisting of bacterium, oomycetes, fungi, and nematodes.

2. The method of claim 1 wherein the phytopathogen is the bacterium *Candidates* 'Liberibacter asiaticus'.

3. The method of claim 1 wherein the composition comprises between 0.01 μM and 5 μM of said compound.

4. The method of claim 1 wherein the compound is applied to the plants once or twice a month.

5. A composition comprising at least one compound of formula III or its salts and an appropriate excipient or carrier, (III)

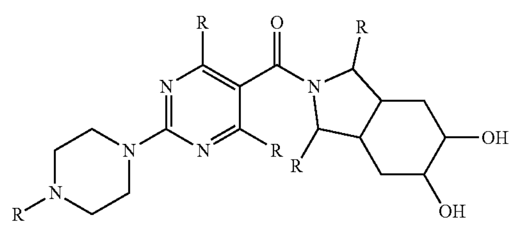

wherein:

R is selected from the group consisting of hydrogen, hydroxyl, halogen, alkyl $C_{1-12}$, heteroalkyl $C_{1-12}$, cycloalkyl $C_{3-7}$, heterocycloalkyl $C_{3-7}$, aryl, heteroaryl, arylalkyl $C_{1-3}$, heteroarylalkyl $C_{1-3}$, arylcycloalkyl $C_{1-7}$, heteroarylcycloalkyl $C_{1-7}$, alkyl $C_{1-3}$ cycloalkyl $C_{3-7}$, and heteroalkyl $C_{1-3}$ cycloalkyl $C_{3-7}$.

6. The composition of claim 5 wherein the compound of formula III is in the range of 0.01 μM-5 μM.

7. The composition of claim 6 characterized for being applied to the plants for the treatment of the disease caused by the bacterium *Candidatus* 'Liberibacter asiaticus'.

8. A method for the stimulation of the natural defense and the induction of resistance against plant diseases comprising applying to plants an effective amount of a composition comprising at least one compound of formula III or its salts,

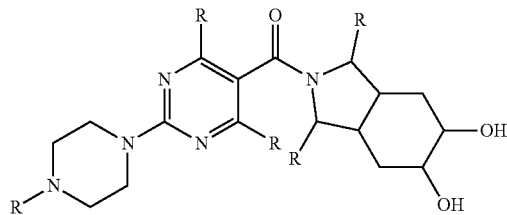

wherein:

R is selected from the group consisting of hydrogen, hydroxyl, halogen, alkyl $C_{1-12}$, heteroalkyl $C_{1-12}$, cycloalkyl $C_{3-7}$, heterocycloalkyl $C_{3-7}$, aryl, heteroaryl, arylalkyl $C_{1-3}$, heteroarylalkyl $C_{1-3}$, arylcycloalkyl $C_{1-7}$, heteroarylcycloalkyl $C_{1-7}$, alkyl $C_{1-3}$ cycloalkyl $C_{3-7}$, and heteroalkyl $C_{1-3}$ cycloalkyl $C_{3-7}$;

wherein the plant disease is caused by a phytopathogen selected from the group consisting of bacteria, oomycetes, fungi, and nematodes.

9. The method of claim 8 wherein the phytopathogen is the bacterium *Candidates* 'Liberibacter *asiaticus*'.

10. A method for the reducing of plant diseases comprising application to the plants of an effective amount of a composition comprising at least one compound of formula III or its salts,

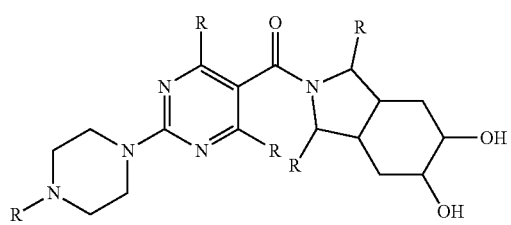

wherein:

R is selected from the group consisting of hydrogen, hydroxyl, halogen, alkyl $C_{1-12}$, heteroalkyl $C_{1-12}$, cycloalkyl $C_{3-7}$, heterocycloalkyl $C_{3-7}$, aryl, heteroaryl, arylalkyl $C_{1-3}$, heteroarylalkyl $C_{1-3}$, arylcycloalkyl $C_{1-7}$, heteroarylcycloalkyl $C_{1-7}$, alkyl $C_{1-3}$cycloalkyl $C_{3-7}$, and heteroalkyl $C_{1-3}$ cycloalkyl $C_{3-7}$;

wherein the plant disease is caused by a phytopathogen selected from the group consisting of bacterium, oomycetes, fungi, and nematodes.

11. The method of claim 10 wherein the phytopathogen is the bacterium *Candidates* 'Liberibacter asiaticus'.

12. The method of claim 10 wherein the composition comprises between 0.01 µM and 5 µM of said compound.

13. The method of claim 10 wherein the compound is applied to the plants once or twice a month.

14. The method of claim 1 wherein the compound of formula III is selected from the groups consisting of

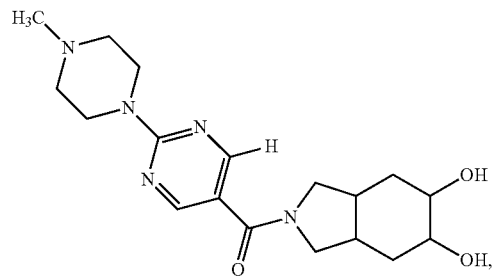

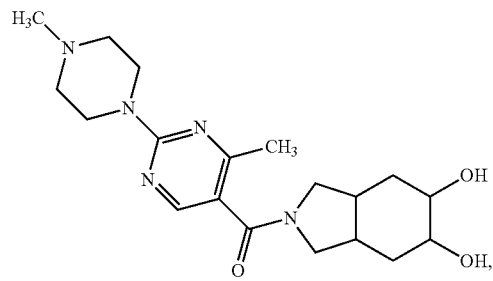

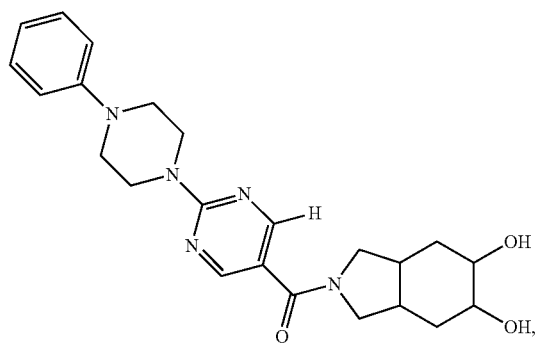

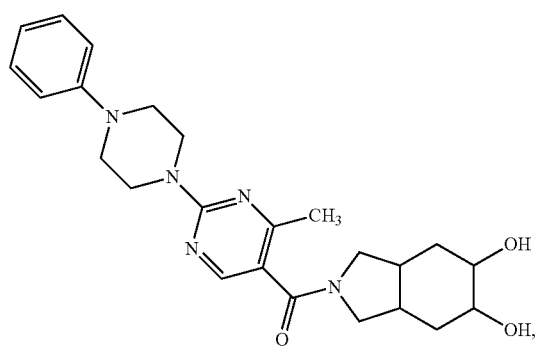

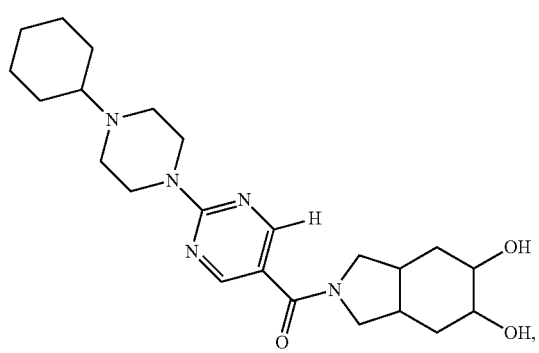

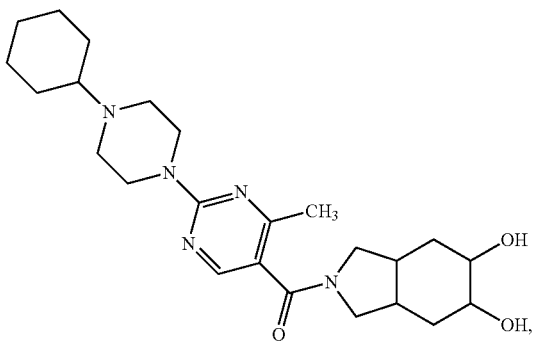
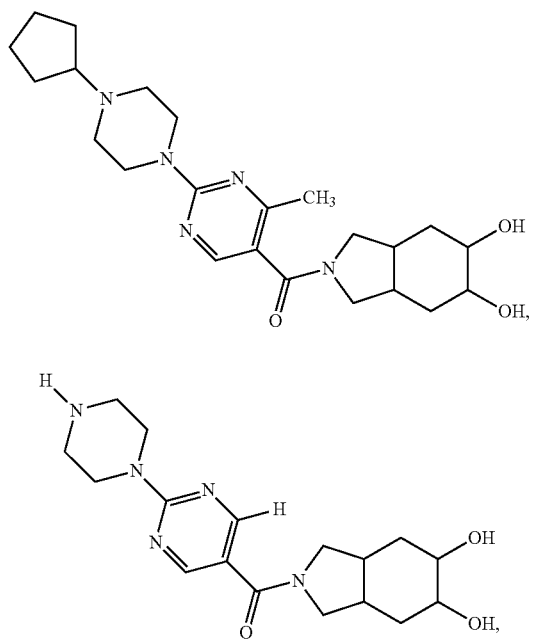
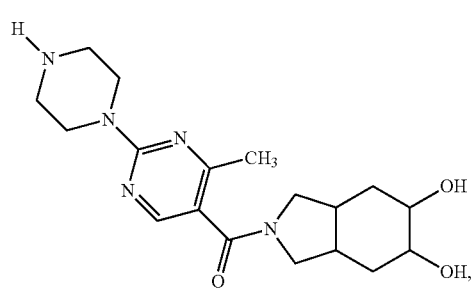
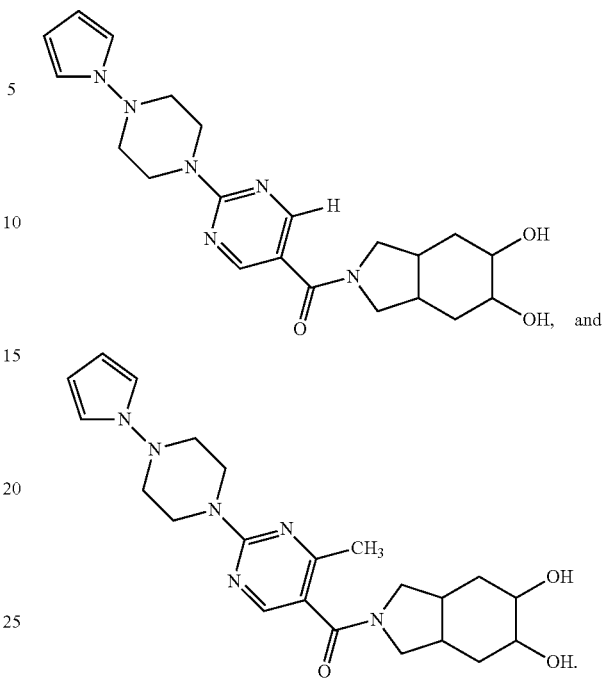
15. The composition of claim 5 wherein the compound of formula III is selected from the groups consisting of
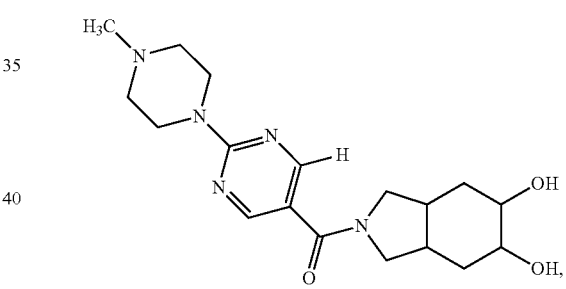
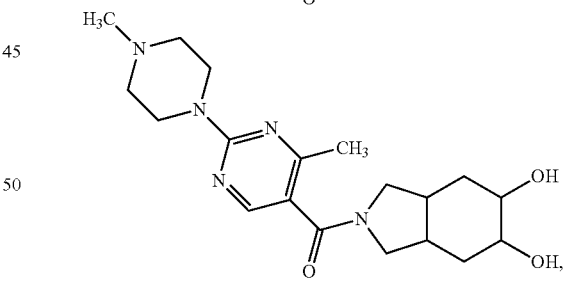
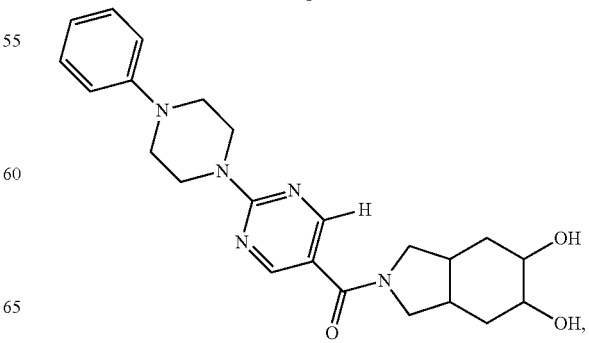

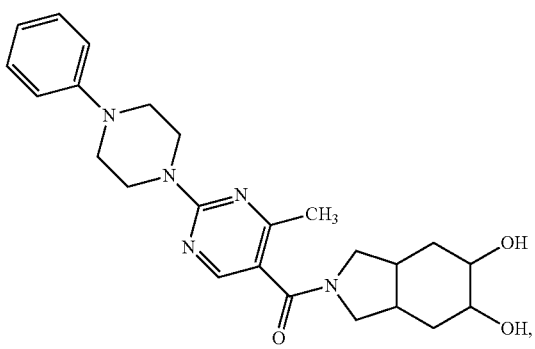
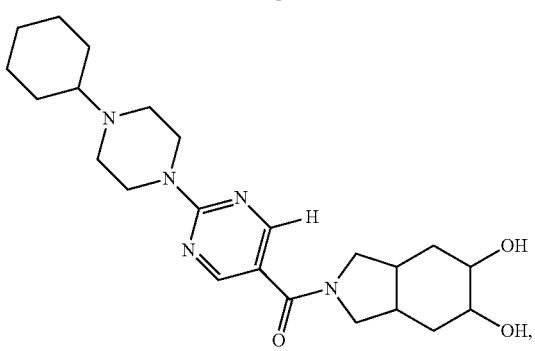
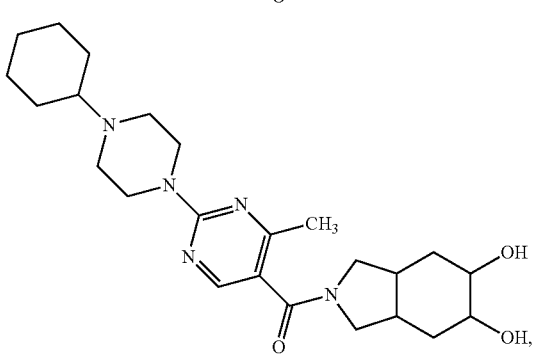
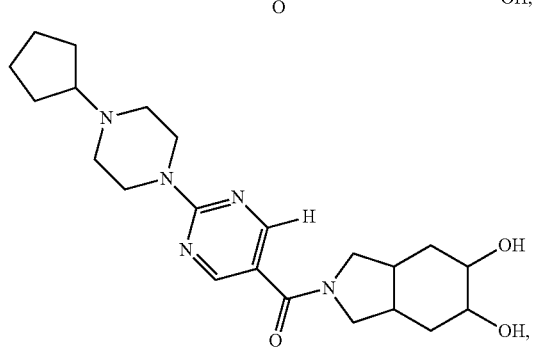
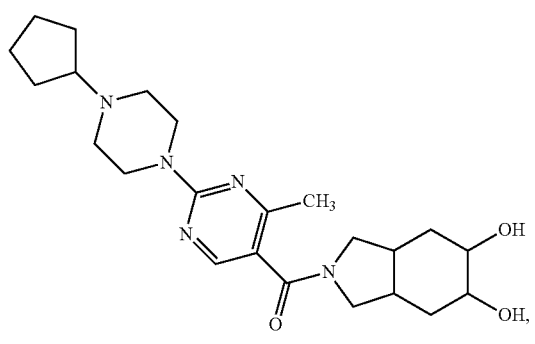
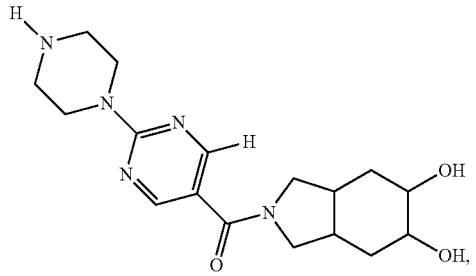
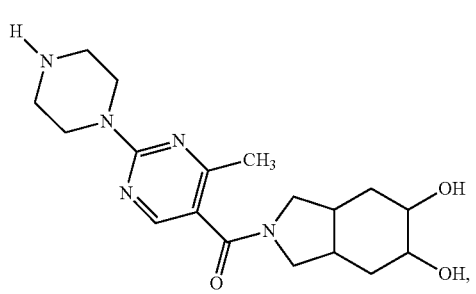
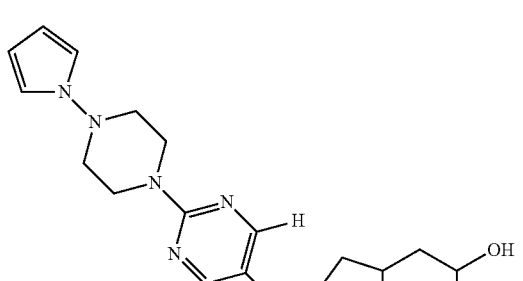
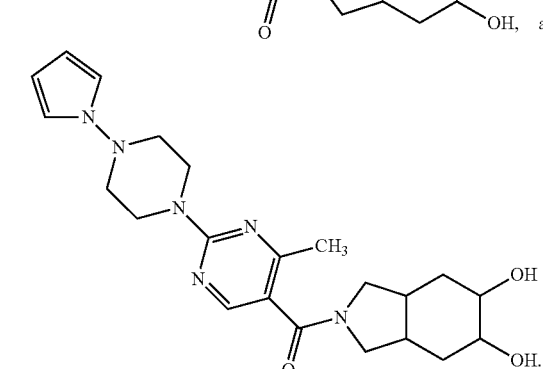
16. The method of claim 8 wherein the compound of formula III is selected from the groups consisting of
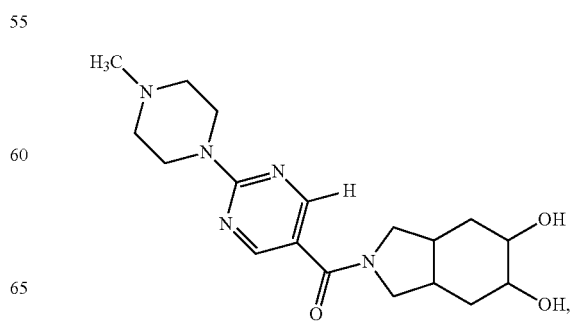

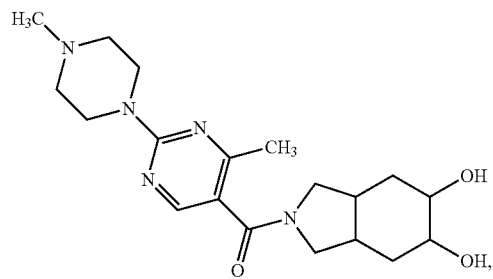
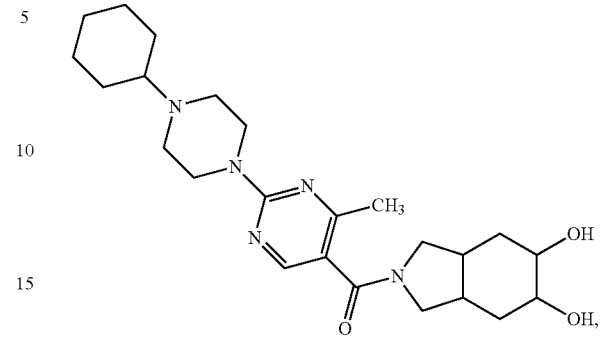
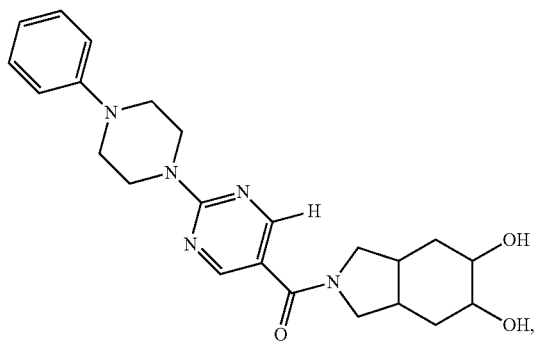
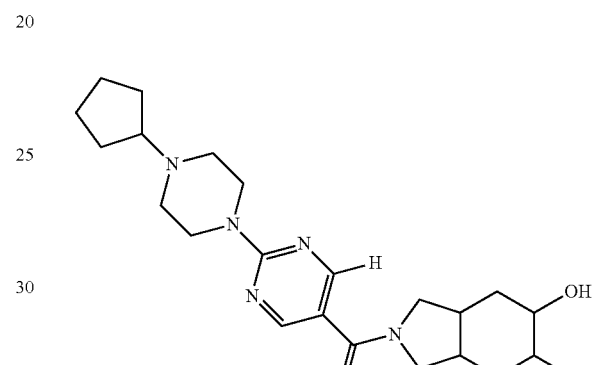
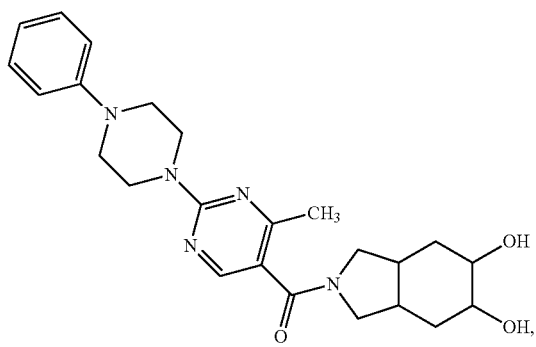
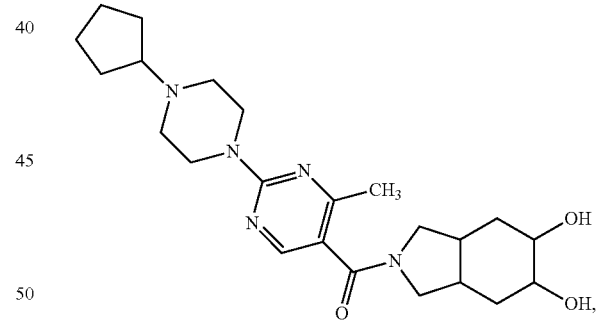
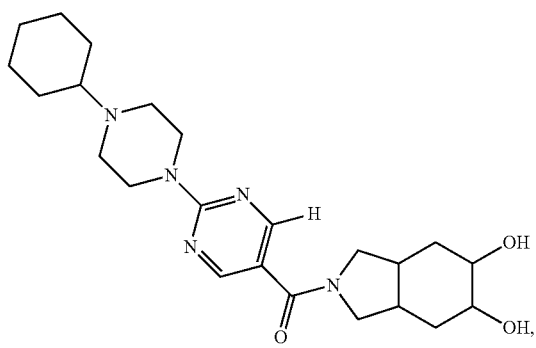
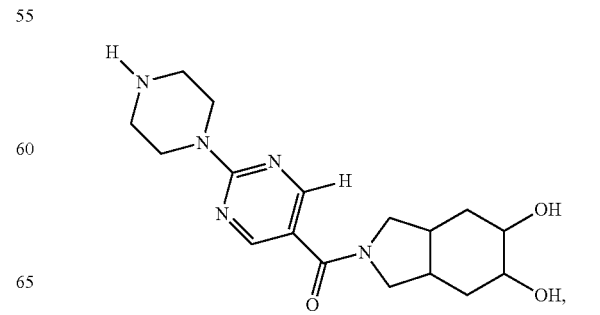

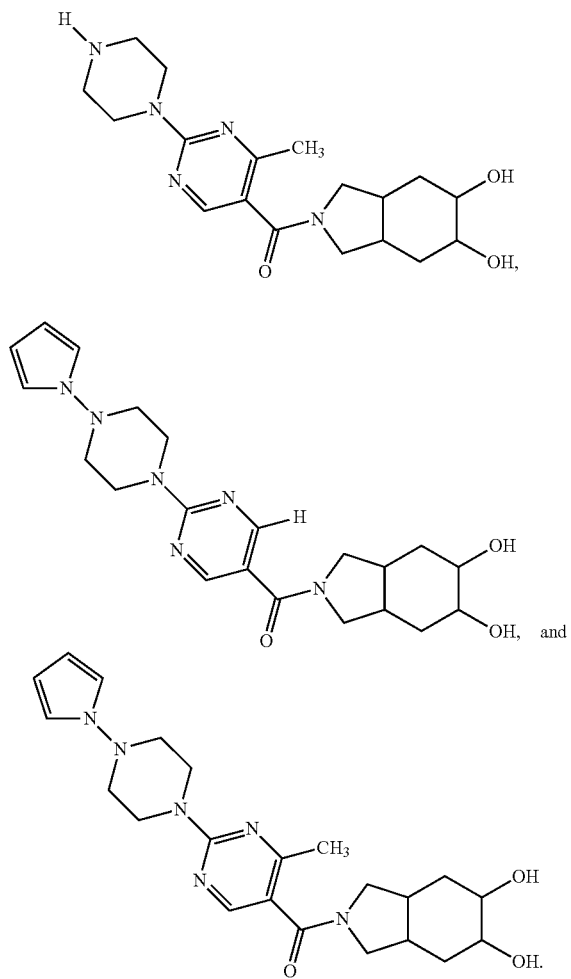
17. The method of claim 10 wherein the compound of formula III is selected from the groups consisting of
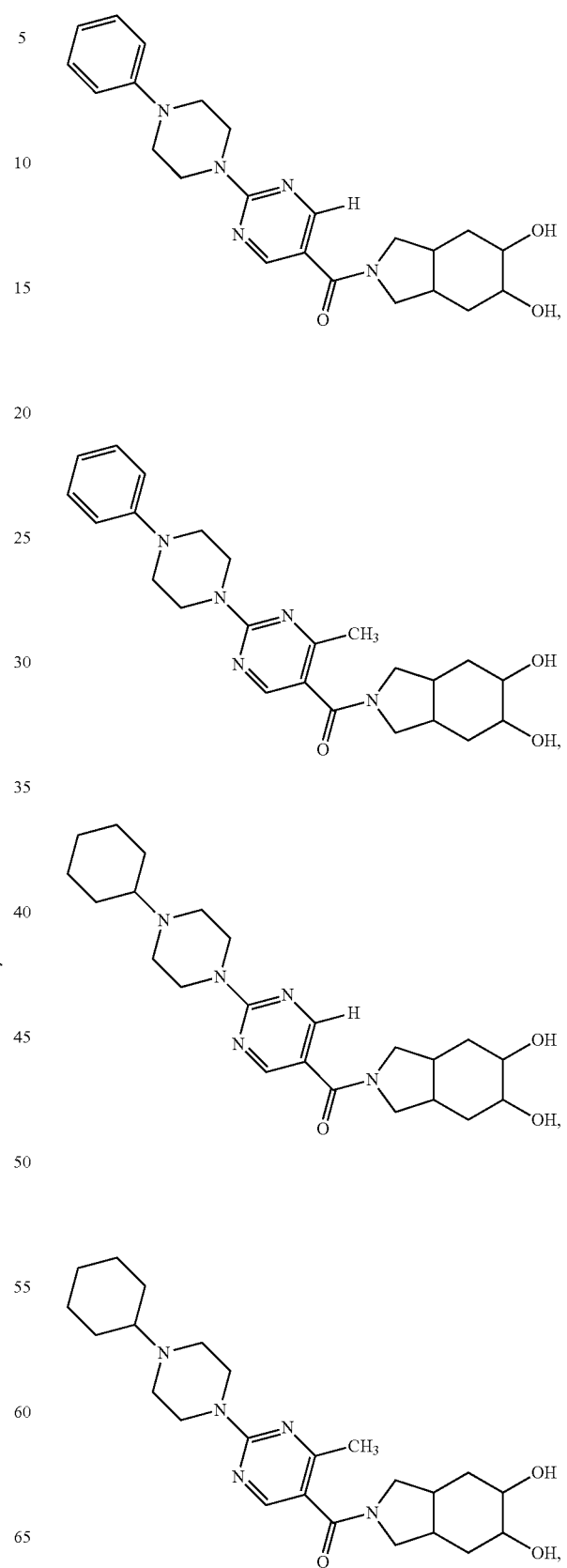

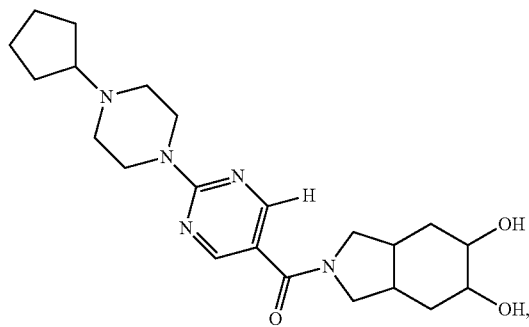

UNITED STATES PATENT AND TRADEMARK OFFICE
CERTIFICATE OF CORRECTION

PATENT NO. : 11,013,235 B2
APPLICATION NO. : 16/752214
DATED : May 25, 2021
INVENTOR(S) : Guirola Cruz et al.

Page 1 of 1

It is certified that error appears in the above-identified patent and that said Letters Patent is hereby corrected as shown below:

In the Specification

Column 3, Lines 52-55:
Now Reads:
Examples of divalent alkyl radicals include, but are not limited to, —CH2CH2CH2CH2-; —CH2CH=CHCH2-; —CH2C=CCH2-; —CH2CH2CH(CH2CH2CH3)CH2- and others.
Should Read:
Examples of divalent alkyl radicals include, but are not limited to, —CH2CH2CH2CH2—; —CH2CH=CHCH2—; —CH2C≡CCH2—; —CH2CH2CH(CH2CH2CH3)CH2— and others.

Column 4, Lines 11-13:
Now Reads:
Examples of divalent heteroalkyl included, but are not limited to, —CH2-CH2-S—CH2-CH2- and —CH2-S—CH2-CH2-NH—CH2-.
Should Read:
Examples of divalent heteroalkyl included, but are not limited to, —CH2—CH2—S—CH2—CH2— and —CH2—S—CH2—CH2—NH—CH2—.

Column 40, Line 30:
Now Reads:
formulas I to V, or theft salts, for the
Should Read:
formulas I to V, or their salts, for the Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*